United States Patent [19]
Venton et al.

[11] Patent Number: 5,814,460
[45] Date of Patent: *Sep. 29, 1998

[54] METHOD FOR GENERATING AND SCREENING USEFUL PEPTIDES

[75] Inventors: Duane L. Venton, Lombard; Anton J. Hopfinger, Lake Forest; Guy Lebreton, Oak Park, all of Ill.

[73] Assignee: Diatide, Inc., Londonderry, N.H.

[ * ] Notice: The term of this patent shall not extend beyond the expiration date of Pat. No. 5,366,862.

[21] Appl. No.: 387,749

[22] PCT Filed: Aug. 9, 1993

[86] PCT No.: PCT/US93/08231
§ 371 Date: Feb. 21, 1995
§ 102(e) Date: Feb. 21, 1995

[87] PCT Pub. No.: WO94/04558
PCT Pub. Date: Mar. 3, 1994

Related U.S. Application Data

[63] Continuation-in-part of Ser. No. 932,200, Aug. 21, 1992, Pat. No. 5,366,862, which is a continuation-in-part of Ser. No. 813,315, Aug. 21, 1991, abandoned, which is a continuation-in-part of Ser. No. 480,865, Feb. 14, 1990, abandoned.

[51] Int. Cl.$^6$ .................................................. G01N 33/53
[52] U.S. Cl. ......................... 435/7.1; 435/23; 435/68.1; 436/501; 436/518; 530/338; 530/343
[58] Field of Search .............................. 435/7.1, 23, 971, 435/68.1; 436/501, 538, 518, 542, 329; 530/333, 338, 343

[56] References Cited

U.S. PATENT DOCUMENTS 5,366,862  11/1994  Venton et al. ........................ 435/7.1

FOREIGN PATENT DOCUMENTS 8701374  3/1987  WIPO .

*Primary Examiner*—Lora M. Green
*Attorney, Agent, or Firm*—Iver P. Cooper

[57] ABSTRACT

The invention allows the generation and screening of a large population of peptides for the presence of peptides which bind a particular macromolecule or macromolecular complex with high affinity, and further allows the favored net synthesis of analyzable quantities of such peptides, by using is the "trap" a macromolecule or macromolecular complex for which binding of the peptide is desired. The starting mixture is preferably spiked with a peptide having some affinity for the target macromolecule so that mutation of the spike or "lead" peptide is favored. The development of improved binding peptides through scrambling may be dynamically monitored by initially binding the target with an insolubilized ligand, and then looking for an increase in the concentration of the target in the soluble phase as a result of the displacement of the reference ligand by scrambled peptides.

24 Claims, 18 Drawing Sheets

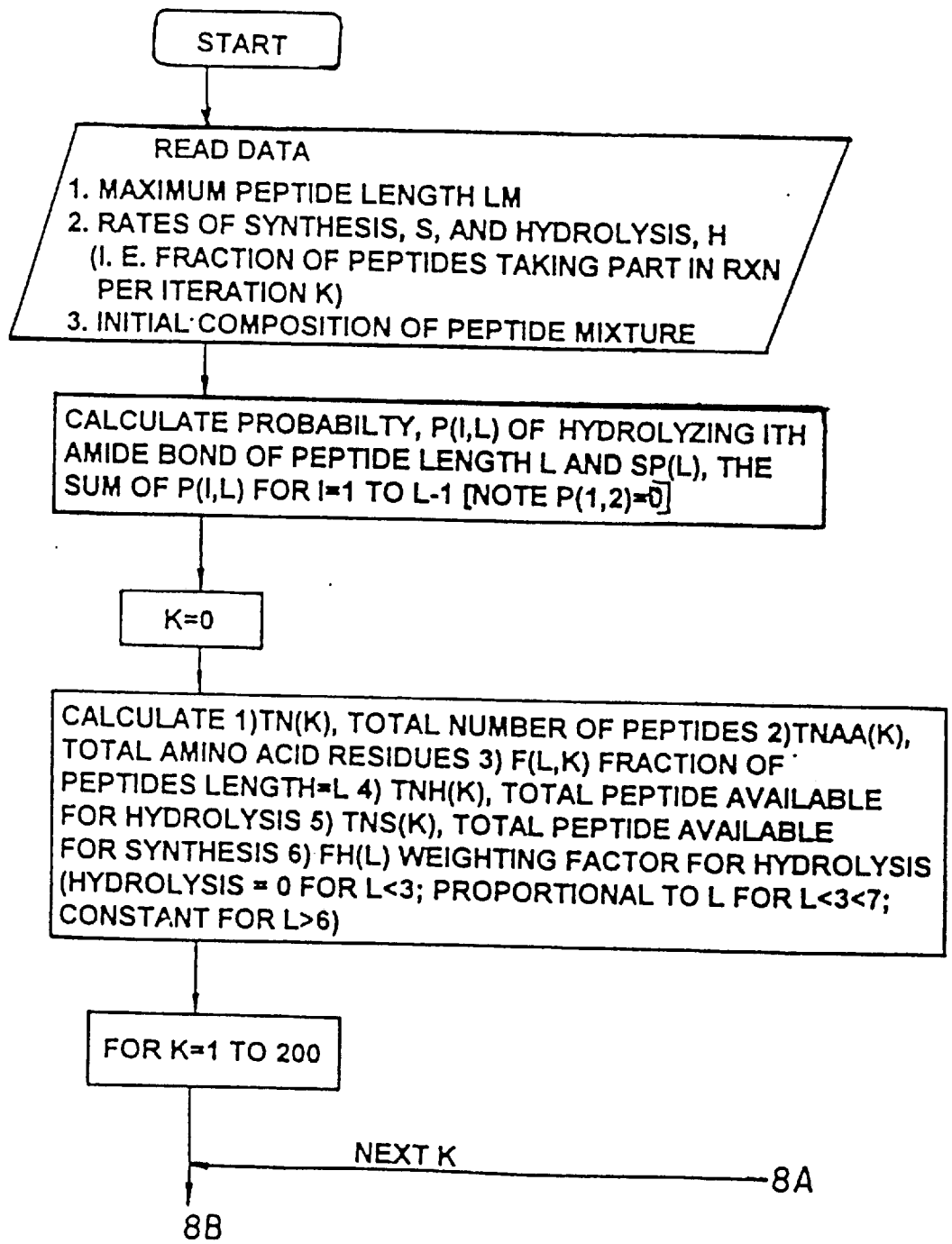
FIG. 8.A

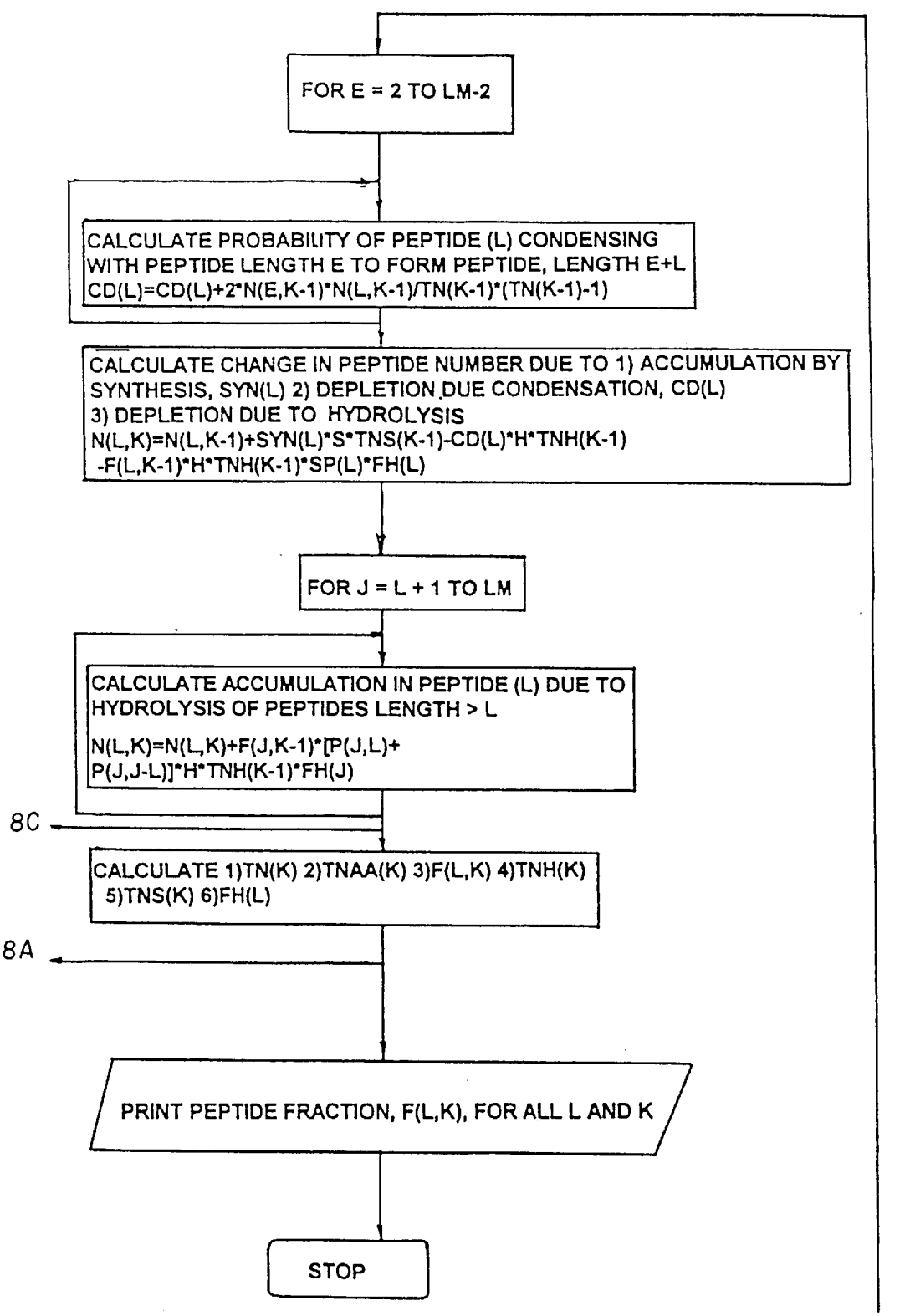
FIG. 8.C

SEQUENCE LISTING ( 1 ) GENERAL INFORMATION:

( i i i ) NUMBER OF SEQUENCES: 20

( 2 ) INFORMATION FOR SEQ ID NO:1:

( i ) SEQUENCE CHARACTERISTICS:
        ( A ) LENGTH: 4 amino acids
        ( B ) TYPE: amino acid (C) STRANDEDNESS: single
        (D) TOPOLOGY: linear (i i) MOLECULE TYPE: peptide (x i) SEQUENCE DESCRIPTION: SEQ ID NO:1:

Arg    Gly    Asp    Trp
    1

(2) INFORMATION FOR SEQ ID NO:2:

(i) SEQUENCE CHARACTERISTICS:
        (A) LENGTH: 4 amino acids
        (B) TYPE: amino acid
        (C) STRANDEDNESS: single
        (D) TOPOLOGY: linear (i i) MOLECULE TYPE: peptide (x i) SEQUENCE DESCRIPTION: SEQ ID NO:2:

Tyr    Tyr    Tyr    Tyr
    1

(2) INFORMATION FOR SEQ ID NO:3:

(i) SEQUENCE CHARACTERISTICS:
        (A) LENGTH: 6 amino acids
        (B) TYPE: amino acid
        (C) STRANDEDNESS: single
        (D) TOPOLOGY: linear (i i) MOLECULE TYPE: peptide (x i) SEQUENCE DESCRIPTION: SEQ ID NO:3:

Asp    Lys    Pro    Asp    Asn    Phe
    1                           5

(2) INFORMATION FOR SEQ ID NO:4:

(i) SEQUENCE CHARACTERISTICS:
        (A) LENGTH: 4 amino acids
        (B) TYPE: amino acid
        (C) STRANDEDNESS: single
        (D) TOPOLOGY: linear (i i) MOLECULE TYPE: peptide (x i) SEQUENCE DESCRIPTION: SEQ ID NO:4:

Arg    Gly    Asp    Tyr
    1

(2) INFORMATION FOR SEQ ID NO:5:

(i) SEQUENCE CHARACTERISTICS:
        (A) LENGTH: 4 amino acids
        (B) TYPE: amino acid
        (C) STRANDEDNESS: single
        (D) TOPOLOGY: linear (i i) MOLECULE TYPE: peptide (x i) SEQUENCE DESCRIPTION: SEQ ID NO:5:

Arg    Gly    Asp    Met
    1

(2) INFORMATION FOR SEQ ID NO:6:

(i) SEQUENCE CHARACTERISTICS:
        (A) LENGTH: 4 amino acids
        (B) TYPE: amino acid (C) STRANDEDNESS: single
(D) TOPOLOGY: linear (i i) MOLECULE TYPE: peptide (x i) SEQUENCE DESCRIPTION: SEQ ID NO:6:

Gly Pro Arg Pro
1

(2) INFORMATION FOR SEQ ID NO:7:

(i) SEQUENCE CHARACTERISTICS:
(A) LENGTH: 4 amino acids
(B) TYPE: amino acid
(C) STRANDEDNESS: single
(D) TOPOLOGY: linear (i i) MOLECULE TYPE: peptide (x i) SEQUENCE DESCRIPTION: SEQ ID NO:7:

Gly Pro Arg Val
1

(2) INFORMATION FOR SEQ ID NO:8:

(i) SEQUENCE CHARACTERISTICS:
(A) LENGTH: 4 amino acids
(B) TYPE: amino acid
(C) STRANDEDNESS: single
(D) TOPOLOGY: linear (i i) MOLECULE TYPE: peptide (x i) SEQUENCE DESCRIPTION: SEQ ID NO:8:

Gly Pro Arg Leu
1

(2) INFORMATION FOR SEQ ID NO:9:

(i) SEQUENCE CHARACTERISTICS:
(A) LENGTH: 4 amino acids
(B) TYPE: amino acid
(C) STRANDEDNESS: single
(D) TOPOLOGY: linear (i i) MOLECULE TYPE: peptide (x i) SEQUENCE DESCRIPTION: SEQ ID NO:9:

Gly Pro Arg Phe
1

(2) INFORMATION FOR SEQ ID NO:10:

(i) SEQUENCE CHARACTERISTICS:
(A) LENGTH: 4 amino acids
(B) TYPE: amino acid
(C) STRANDEDNESS: single
(D) TOPOLOGY: linear (i i) MOLECULE TYPE: peptide (x i) SEQUENCE DESCRIPTION: SEQ ID NO:10:

Arg Gly Asp Phe
1

(2) INFORMATION FOR SEQ ID NO:11:

(i) SEQUENCE CHARACTERISTICS:
(A) LENGTH: 6 amino acids
(B) TYPE: amino acid ( C ) STRANDEDNESS: single
( D ) TOPOLOGY: linear ( i i ) MOLECULE TYPE: peptide ( x i ) SEQUENCE DESCRIPTION: SEQ ID NO:11:

Gly Arg Gly Asp Ser Pro
1               5

( 2 ) INFORMATION FOR SEQ ID NO:12:

( i ) SEQUENCE CHARACTERISTICS:
( A ) LENGTH: 13 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:12:

Thr Cys Val Xaa Asn Lys Tyr Phe Ser Asn Ile His Trp
1               5                   10

( 2 ) INFORMATION FOR SEQ ID NO:13:

( i ) SEQUENCE CHARACTERISTICS:
( A ) LENGTH: 13 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:13:

Thr Thr Phe Lys Arg Ile Phe Leu Lys Arg Met Pro Ser
1               5                   10

( 2 ) INFORMATION FOR SEQ ID NO:14:

( i ) SEQUENCE CHARACTERISTICS:
( A ) LENGTH: 11 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:14:

Arg Ile Phe Leu Lys Arg Met Pro Ser Ile Arg
1               5                   10

( 2 ) INFORMATION FOR SEQ ID NO:15:

( i ) SEQUENCE CHARACTERISTICS:
( A ) LENGTH: 4 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:15:

Thr Asn Tyr Thr
1

( 2 ) INFORMATION FOR SEQ ID NO:16:

( i ) SEQUENCE CHARACTERISTICS:
( A ) LENGTH: 12 amino acids
( B ) TYPE: amino acid (C) STRANDEDNESS: single
(D) TOPOLOGY: linear (ii) MOLECULE TYPE: peptide (xi) SEQUENCE DESCRIPTION: SEQ ID NO:16:

Met Leu Phe Ile Leu Ile Lys Arg Ser Arg His Phe
1               5                   10

(2) INFORMATION FOR SEQ ID NO:17:

(i) SEQUENCE CHARACTERISTICS:
    (A) LENGTH: 8 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:17:

Val Ala Ile Thr Val Leu Val Lys
1               5

(2) INFORMATION FOR SEQ ID NO:18:

(i) SEQUENCE CHARACTERISTICS:
    (A) LENGTH: 6 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:18:

Trp Thr Val Pro Thr Ala
1               5

(2) INFORMATION FOR SEQ ID NO:19:

(i) SEQUENCE CHARACTERISTICS:
    (A) LENGTH: 9 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:19:

Gly Ala Val Ser Thr Ala Arg Gly Asp
1               5

(2) INFORMATION FOR SEQ ID NO:20:

(i) SEQUENCE CHARACTERISTICS:
    (A) LENGTH: 8 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:20:

Glu Gly Val Tyr Val His Pro Val
1               5

METHOD FOR GENERATING AND SCREENING USEFUL PEPTIDES

This application is a continuation in part of Ser. No. 07/932,200, filed Aug. 21, 1992, now U.S. Pat. No. 5,366, 862, which is a continuation in part of Ser. No. 07/813,315, filed Aug. 21, 1991, now abandoned, which is a continuation-in-part of PCT application PCT/US91/00891, filed Feb. 14, 1991, designating the United States, which is a continuation-in-part of U.S. Ser. No. 07/480,865, filed Feb. 14, 1990, now abandoned, all incorporated by reference herein.

BACKGROUND OF THE INVENTION

1. Field of the Invention

The invention relates to novel methods for generating and screening peptides which are useful for a variety of applications.

2. Description of the Background Art

Small peptides (2–15 amino acids) are capable of possessing unique spatial and thermodynamic properties which allow them to bind specifically to particular proteins. The binding of these peptides to such proteins can transiently or permanently eliminate or activate the function of those proteins. Thus a peptide which binds to, and eliminates the function of a coat protein of a virus could serve as an effective pharmacologic agent against that virus. Similarly, a peptide which binds to and activates a receptor for taste or olfaction could serve as a useful active agent for flavoring or perfumes. There is considerable interest in the pharmaceutical industry in the development of such useful peptides. The major difficulty is that the production and screening of individual peptides is inefficient and labor intensive. Peptides must be made individually and tested for their ability to bind the protein of interest. Because of the difficulty of making and screening each individual peptide, it is not possible to screen large numbers of peptides. There is, therefore, a need for methods which allow for rapid and efficient screening of a large number of peptides. An ideal system would provide for the simultaneous synthesis and screening of every possible peptide of a particular size.

A variety of proteolytic enzymes, including trypsin, chymotrypsin, pepsin, papain, bromelain, thermolysin and *S. griseus* proteinase, hydrolyze peptide bonds. The rate of hydrolysis is influenced by temperature, substrate and enzyme concentration, enzyme specificity, and substrate sequence. *S. griseus* proteinase, papain, and the subtilisin enzymes are known to have broad substrate specificity, but for total enzymatic hydrolysis, the use of a mixture of enzymes is preferred. Hill, "Hydrolysis of Proteins", in *Advances in Protein Chemistry*, 20: 37, 89–90 (Anfinsen, Jr , et al., eds., 1965).

In 1937, it was demonstrated that a proteolytic reaction could be reversed. Soon thereafter, proteases were used for both stepwise and fragment condensation synthesis of peptides of predetermined sequence. Since the enzymes differed in terms of which peptide bonds would be formed, several different enzymes had to be used in succession to make oligopeptides. Unfortunately, enzymatic chain elongation could endanger preexisting bonds. See Sakina, et al., *Int. J. Peptide Protein Res.*, 31: 245–52 (1988); Kullman, *Proc. Nat. Acad. Sci.* (U.S.A.) 79: 2840–44 (1982).

One problem in enzymatic synthesis of peptides is that hydrolysis is thermodynamically favored under normal conditions. Thus, the equilibrium must be shifted. Homandberg, et al., Biochemistry, 21: 3385–8 (1982) teaches that one may use a "molecular trap", that is, a molecule which has an affinity for a particular peptide of known amino acid sequence, to shift the equilibrium to favor the synthesis of such a peptide.

Varied approaches have been utilized for the purpose of generating diverse populations of peptides.

"Semisynthetic" peptides and proteins have been prepared by (1) limited proteolysis of naturally occurring polypeptides to yield a workable set of fragments, (2) chemical synthesis of an additional oligopeptide, and (3) reconstruction of synthetic and native partners. The technique is typically used to prepare analogues of naturally occurring polypeptides. Chaiken, *CRC Critical Reviews in Biochemistry*, 255 (September 1981). Ruggeri, et al., *P.N.A.S.* (*U.S.A.*), 83: 5708–12 (August 1986) prepared a series of synthetic peptides in lengths up to 16 residues that were modeled on various platelet-binding peptides. The technique used was one of solid state synthesis by chemical means, but using individual compartmentalized peptide resins to impart the desired variety. See Houghten, et al., *P.N.A.S.* (*U.S.A.*), 82: 5131–35 (1985). Yet another approach to generating a variety of peptides is through expression of mixed oligonucleotides. See Goff, et al., *DNA*, 6: 381–88 (1987). None of these approaches involve a balanced equilibrium between random synthesis and random degradation within a large population of peptides. Instead, a known peptide is cleaved at a known site, a known amino acid or peptide fragment is conjugated to the first peptide at that cleavage site, and so forth. What is needed is such a scrambling system, wherein a diverse population of peptides is sampled for binding activity and selective removal of a particular peptide having a desired binding activity but a then-unknown amino acid sequence will result in net selective synthesis of that product without net synthesis of large amounts of every possible product.

The primary use for proteolytic enzymes as catalysts for peptide synthesis has previously been directed toward the synthesis of single, known peptide species. Several patents relate to such enzymatic synthesis of non-random peptides and, to this end, disclose and claim use of protective groups to prevent formation of other peptides. Isowa, U.S. Pat. No. 3,977,773 (1976) relates to use of pepsin in the enzymatic production of peptides containing three or more amino acids. Certain constraints are set on the sequence of the peptide. N- and C-terminal protective groups are broadly recited. Isowa, U.S. Pat. No. 4,086,136 (1978) claims the use of a thiol proteinase (e.g., papain) or a serine proteinase (e.g., subtilisin) in the enzymatic synthesis of peptides containing two or more amino acids. The claim requires that one amino acid or peptide carry an amino protective group and the other a carboxyl protective group, and the latter be one of the following: tertiary alkoxy, benzyloxy, benzylamino, and benzylhydrylamino. Isowa, U.S. Pat. No. 4,116,768 (1978) is drawn to production of a peptide under the action of a metalloproteinase enzyme. N- and C-terminal protective groups are broadly recited. See also Isowa, U.S. Pat. No. 4,119,493 (1978). Isowa, U.S. Pat. No. 4,165,311 (1979) is essentially directed to addition compounds for use in the production of alpha-L-aspartyl-L-phenylalanine alkyl esters (i.e., aspartame-like compounds). Isowa, U.S. Pat. No. 4,256,836 (1981) is drawn to the process for the production of these compounds using a protease. See also U.S. Pat. No. 4,521,514 (1985).

Johansen, U.S. Pat. No. 4,339,534 (1982; De Forened Bryggerier A/S) is broadly directed to the use of an L-specific serine or thiol carboxypeptidase, such as yeast carboxypeptidase, for enzymatic synthesis of peptides. See also Johansen, U.S. Pat. No. 4,806,473. Oyama, U.S. Pat. No. 4,521,514 (1985; Toyo Soda) is directed to a process for recovering protease. Snellman, U.S. Pat. No. 3,544,426 (1965) relates to synthesis of peptide chains by reaction of a carboxylic acid ester, an amine (including a peptide), a phosphoric derivative of a nucleoside, and an enzyme. Morihara, U.S. Pat. Nos. 4,320,197 and 4,320,196 relate to a semisynthesis of human insulin.

Of course, the use of proteolytic enzymes to generate peptides of exclusively pre-existing amino acid sequences through simple degradation of existing proteins is well known. For example, Matsukawa, U.S. Pat. No. 3,855,196 (issued Dec. 17, 1974 to the inventors) decomposes the skeletal muscles of a cervoidae (a taxon including reindeer and caribou) with a protease into low molecular weight peptides with a molecular weight of less than 1,000. These peptides are separated from the crude digest using a gel-type molecular sieve.

Maubois, U.S. Pat. No. 3,993,636 (issued Nov. 23, 1976 to the Institute National de la Recherche Agronomique) ultrafiltered vegetable proteins using membranes filtered with molecular weight cutoffs as low as 2,000 (col. 4, lines 38–44).

Fujimaki, U.S. Pat. No. 3,813,327 (issued Apr. 9, 1974, now expired) claims obtaining an oligopeptide of MW 1,200–2,000 by hydrolyzing a protein with, e.g., subtilisin.

Pieczenik, WO87/01374 further uses such uniform-sized, but variably sequenced peptides derived from simple degradation of existing proteins to identify the recognition sites of antibodies. Alternatively, variable peptides are produced through chemical synthesis from amino acids, or through insertion of fractionated DNA into an expression vector and subsequent expression thereof. Pieczenik does not, however, recognize the advantages of combining random degradation with random synthesis within a chemical system wherein they are in a balanced equilibrium, and disturbing that equilibrium only to favor synthesis of a peptide species that exhibits a desired binding activity.

Binding of peptides by macromolecules in the presence or absence of semi-permeable membranes has previously been described for a variety of purposes. Receptor binding assays are well known in the art, and the screening of peptides for ability to bind to a receptor is conventional. See, e.g., Ruggeri, supra. Westman U.S. Pat. No. 3,649,457 (issued Mar. 14, 1972 to Monsanto Co.) discloses placing a soluble enzyme-polymer conjugate in an enzymatic reaction chamber having a semipermeable wall which permits passage of the enzymatic reaction products but not of the enzyme reagent. In the example, the membrane had an exclusion limit of as low as 1000 (col. 3, lines 15–18). Papain was among the enzymes suggested for use in this system (col. 9, line 48). While the reaction product must be of lower molecular weight than the enzyme-polymer conjugate, "it may be of a higher molecular weight than starting substrate, as when substrate comprises a plurality of reactants which are enzymatically reacted together to give a higher molecular weight product." (col. 13, lines 60–63). Likhite, U.S. Pat. No. 3,843,444 (issued Oct. 23, 1974) discloses a membrane separation process in which a ligand in one medium is attracted across a barrier film to a receptor in a second medium. It must be emphasized that in Likhite's system, neither the receptor nor the ligand actually crosses the barrier; they are selectively collected on opposite sides thereof. (See, e.g., col. 2, lines 20–21, 25–28 and 67–70).

The present invention is directed toward satisfying the need for the generation of large, random populations of peptides of a particular size range and to concomitant selection of potentially useful peptides from such a population and synthesis of analyzable quantities of such peptides without the net production of large quantities of extraneous, random peptides. The invention fills this need by the use of scrambling reactions, i.e., a system at steady state, and preferably at a global equilibrium, between synthesis and degradation of peptides catalyzed by proteolytic enzymes, and by coupling such scrambling reactions to a means for selection and net synthesis of potentially useful peptides through perturbation of the equilibrium, in particular by binding of such peptides by a macromolecule, thus removing such peptides from the system and shifting the equilibrium to favor formation of such bound peptides. Genetically engineered proteins having enzymatic activity are also useful in promoting scrambling reactions and providing random distributions of peptides.

SUMMARY OF THE INVENTION

A method is provided for inexpensively and rapidly producing a large and varied population of peptides, up to nearly all theoretically possible peptides in a particular size range, according to amino acid number and screening this varied population of peptides for the presence of peptides which bind to a target, such as a macromolecule or macromolecular complex, and are thus potentially useful for pharmacologic or other purposes. The method further provides for the generation of analyzable (picomole to millimole) quantities of such peptides without concomitant net synthesis of such quantities of extraneous random peptides.

A full showing of pharmacologic utility of a single peptide isolated from a large, random population of peptides involves the following steps: (1) generation of the peptide, (2) demonstration that a particular peptide binds specifically to a macromolecule associated with a particular physiological function, (3) isolation of the specific binding peptide, (4) determination of the structure (amino acid sequence) of the specific binding peptide, (5) large-scale synthesis of the specific binding peptide, (6) demonstration of biological activity of peptide, and (7) pre-clinical and clinical testing. Satisfactory methods currently exist for steps 3–7. What is needed is a method for generating a large, random population of peptides, screening that population for the presence of peptides which specifically bind a particular protein or macromolecule and synthesizing analyzable quantities of such peptides.

The present invention satisfies this need by employing (1) a "scrambling" system which utilizes one or more proteases to randomly generate large numbers of peptides of a particular size and of varied, undetermined sequences through balanced peptide synthesis and degradation, (2) a molecular trap to drive the synthetic reaction toward completion with respect to only the binding peptide, as well as to screen for the particular peptide(s) of interest, and (3) a semipermeable barrier, covalent or matrix immobilization, or similar means of physically separating the scrambling system from the molecular trap.

One object of the invention is to provide a means for inexpensive and rapid synthesis of very large random populations of peptides.

A second object of the invention is to provide a method for screening such a population for the presence of peptide (s) (specific binding peptides) which bind a particular biologically important macromolecule and to be able to identify such peptide(s) by amino acid sequence.

A third object of the invention is to provide a means for concomitant screening of a large, random population of peptides for the presence of peptide(s) (specific binding peptides) which bind to different biologically important macromolecules in a molecular complex whose properties are different than the same molecules in isolation.

A fourth object of the invention is to provide specific binding peptides of defined amino acid sequence, which having been identified by the methods of the invention, are readily produced by standard synthetic means.

A fifth object of the invention is to permit simultaneous monitoring of multiple binding sites on the same receptor. Because the peptides in our system are free in solution, the receptor can interact with multiple peptide species simultaneously. In certain cases, the binding of peptides at multiple sites could, through conformational changes in the receptor, increase the apparent affinities of each peptide relative to their affinities in a single site interaction. This phenomenon is observed in protein/protein interactions in which multiple binding sites in combination yield extremely high affinities. An example of this is found in the thrombin inhibitor, hirudin, from the leech, *Hirudo medicinalis*. Hirudin binds to thrombin at two sites: the fibrinogen recognition site and the protease active site with a total observed $K_d=10^{-13}M$ (Stone and Hotsteenge, 1986, *Biochemistry*, 25, 4622–4628). Divided into separate sites, hirudin-derived inhibitor peptides binding solely to the fibrinogen recognition site exhibit $K_d$'s of $10^{-9}M$ while those binding to the protease active site have $K_d$'s of about $10^{-6}M$ (Maraganore et al., 1989, *J. Biol. Chem.*, 264 (15), 8692–8698). By contrast, those technologies that employ tethered peptides will be screening each product individually, and thus, cannot take advantage of any situations whereby the presence of more than one binding site on a receptor allows for such interactions of ligands.

A sixth object of the invention is to present peptides to the target in such a manner so that it is unnecessary to verify that, in soluble form, they bind the target. When a peptide is presented such that it is tethered to another entity, the binding of the tethered peptide to the target may be dependent on the presence of the tether. If the tethered entity is not to be a part of the ultimate product, the peptide must be rescreened, without the tether. If the untethered peptides of the present invention are found to bind to a target, there is no need to rescreen them.

A seventh object of the invention is to permit the evaluation of receptors that require solubilizing or micelle-forming detergents to exhibit their ligand binding activity (e.g., membrane-associated receptors). Our method does not employ immobilized or tethered ligands (as do Affymax and Selectide) and consequently, the ligands are not physically restricted in their approach to the receptor. Having the peptides tethered to a solid support raises the possibility that potentially suitable ligands may not have sufficient access to the receptor or may be presented to the receptor in a conformation that doesn't permit binding. This problem is compounded in the case of membrane- or micelle-bound receptors, where the matrix containing the receptor also imposes a physical restriction on the access of ligands. These two restrictions increase the probability that structurally suitable ligands may be missed, or that the actual affinity of some ligands may be underestimated.

In a second embodiment, the contents of the reaction chamber 1 are also pumped by pump 6 through extraction chamber 7 into binding chamber 8. This configuration is useful when the desired peptides are those which bind to target A but not target B. Target B is presented in extraction chamber 7 and Target A in chamber 8. Peptides which bind to target B will be trapped by the extraction chamber 7 and therefore will be presented in substantially reduced concentration to Target A in the binding chamber 8. This provides a sensitive and direct method for identifying highly specific binding peptides. The pump 6 and extraction chamber 7 should provide a sufficiently slow flow rate, and sufficiently large surface area to deplete the reaction chamber 1 contents of those peptides having high affinity for the macromolecule present in 7.

Figure 1:
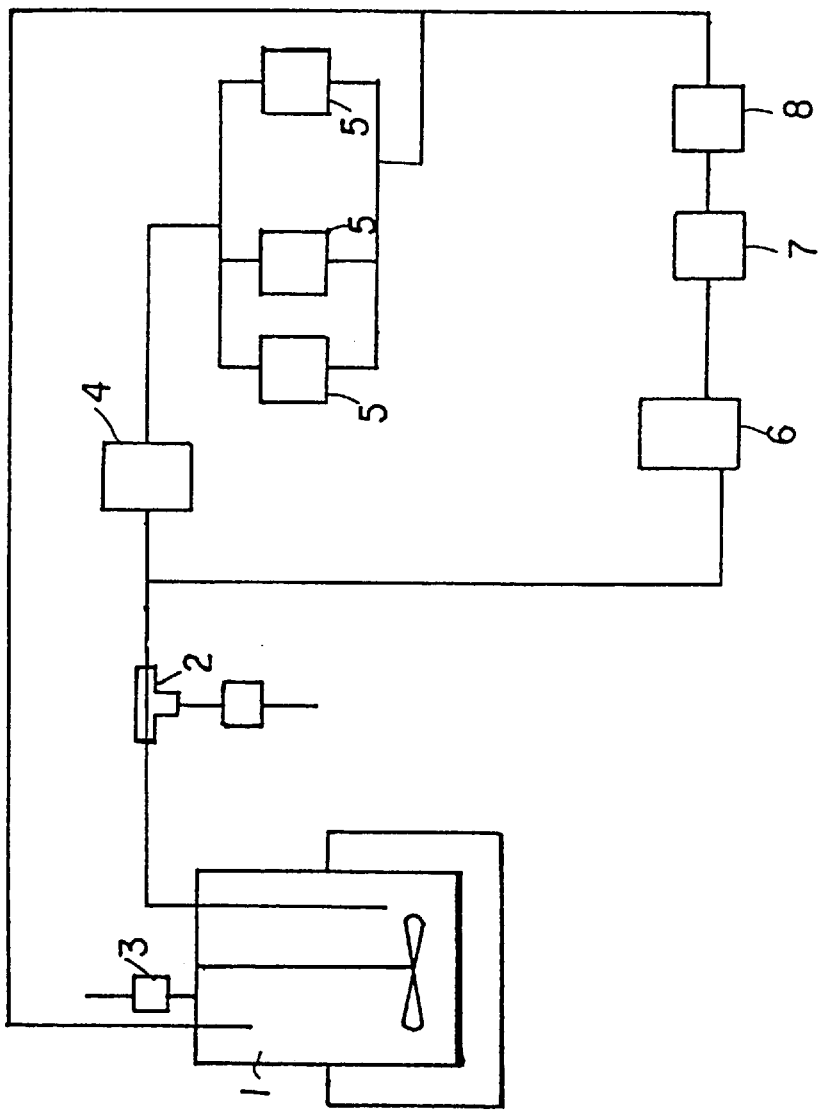
FIG. 1: Schematic drawing of peptide synthesis/trapping equipment and procedures of this invention. The equipment includes a stirred, temperature-controlled, reaction chamber 1, for example a system in which the proteolytic enzymes and starting peptides are placed and the scrambling reaction initiated. To maintain sterility within the reaction chamber, all reagents are added to, and aliquots removed from, the pre-sterilized reaction chamber 1 by way of a micro-filtration device 2, through a three way valve. Pressure is released to the atmosphere by way of a second micro-filtration valve 3. A Gilman bacterial air vent is suitable. Suitable antibacterial agents may also be added to the reaction mixture to inhibit bacterial growth. The contents of the reaction chamber 1 in one embodiment of the invention are circulated by pump 4 through binding chamber 5. The apparatus is assembled with parallel binding chambers 5 to concurrently assay multiple macromolecular sinks and to perform comparative identification of peptides for structurally related macromolecular systems.
Figure 2:
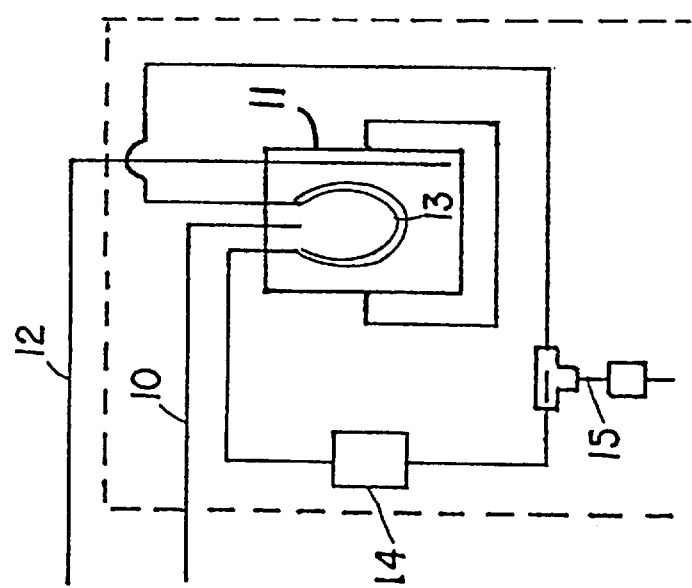

FIG. 2: Detailed illustration of binding chambers 5 and 8, from FIG. 1. The reaction mixture from reaction chamber 1 flows into the binding chamber 11 through line 10 and is returned by line 12.

The macromolecules are circulated through hollow fiber 13 by pump 14.

These fibers, by virtue of their semipermeable nature place the macromolecule in contact with the peptides being generated by the scrambling reaction in the reaction chamber 1 without exposing them to the catabolic environment of this mixture. A valve and micro-filtration device 15 are used on the macromolecule sink side to load the macromolecule sink, and to sample the peptide macromolecule complex. The extraction chamber 7 is similar to the binding chambers described above with the exception that the cell is designed to maximize the contact time with the reaction chamber contents in order to insure depletion of peptides having affinity for the extracted ligand before exit to the binding chamber 8. The macromolecule in 7 is sampled before the complete system reaches equilibrium in order to successfully identify peptides having unique affinity for the macromolecule in 8 relative to that in cell 7. In those cases, where different conditions (temperature, buffers, relative ratios of a.a., peptidases, etc.) are desired, different reaction chamber/binding chamber combinations are used. All binding and extraction chambers may be reused after washing.

Figure 3:
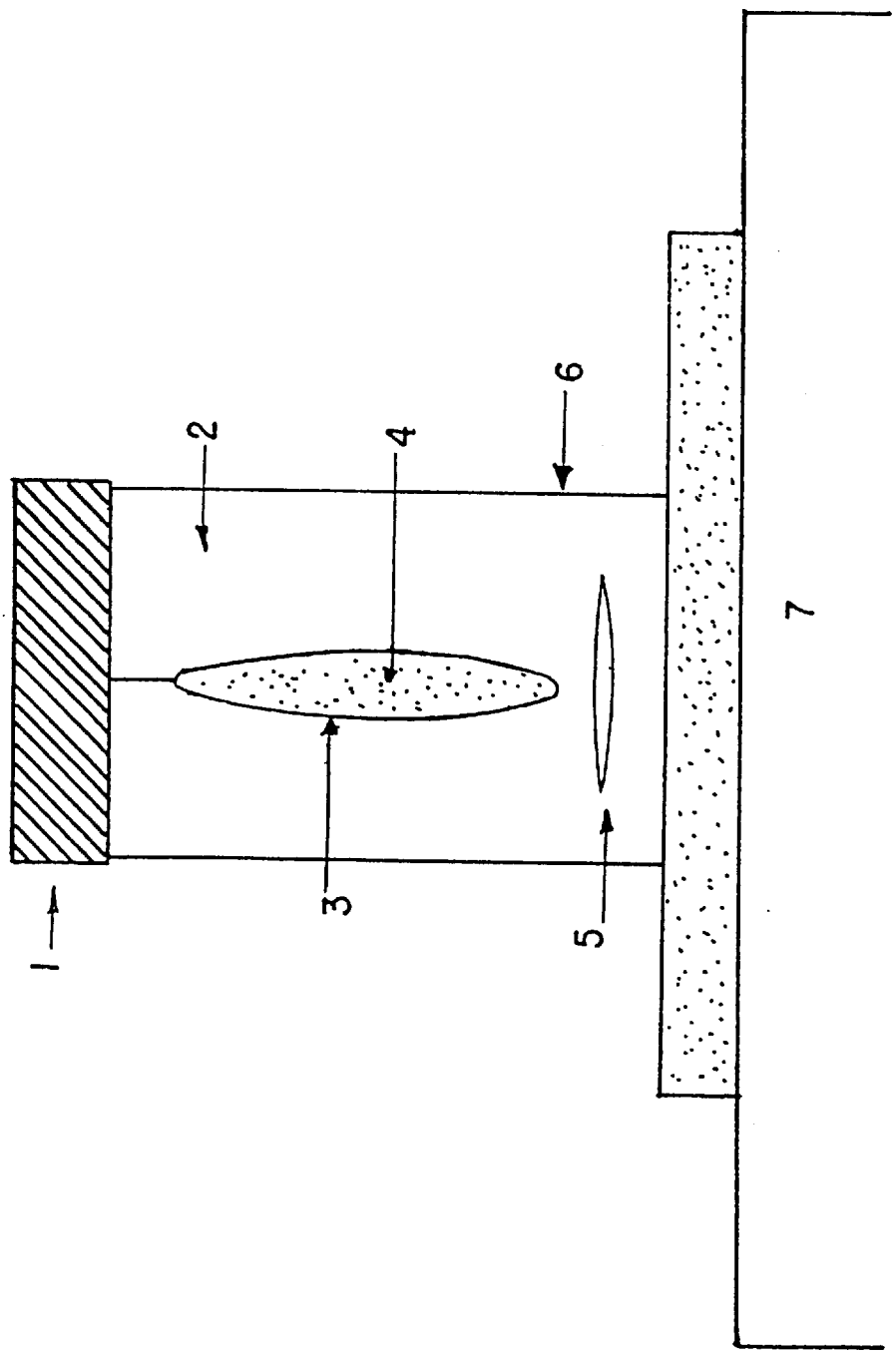

FIG. 3: Schematic of a simple semipermeable membrane-type peptide generating and screening apparatus. 1=cap, 2=scrambling mixture, 3=dialysis bag, 4=macromolecular sink, 5=stir bar, 6=reservoir, and 7=magnetic stirrer. A mixture of protease(s) and substrate (protein(s) and/or peptide(s)) is placed in a holding reservoir (of any practical volume). The macromolecular sink (receptor) is placed in a dialysis bag (approximately one tenth the volume of the holding reservoir and having a molecular cutoff of preferably 1000–3500 daltons). The dialysis bag is immersed in the enzyme-protein-peptide mixture, and low molecular weight peptides generated in this mixture diffuse across the dialysis membrane and interact with the macromolecular sink. After a suitable period of time, the contents of the dialysis bag are removed and evaluated for peptides which have bound to the macromolecule. The binding chamber is sealed with a cap to ensure sterility of the system, and the contents of the reservoir are stirred to ensure adequate mixing of the enzyme, protein, peptide solution.

Figure 4:
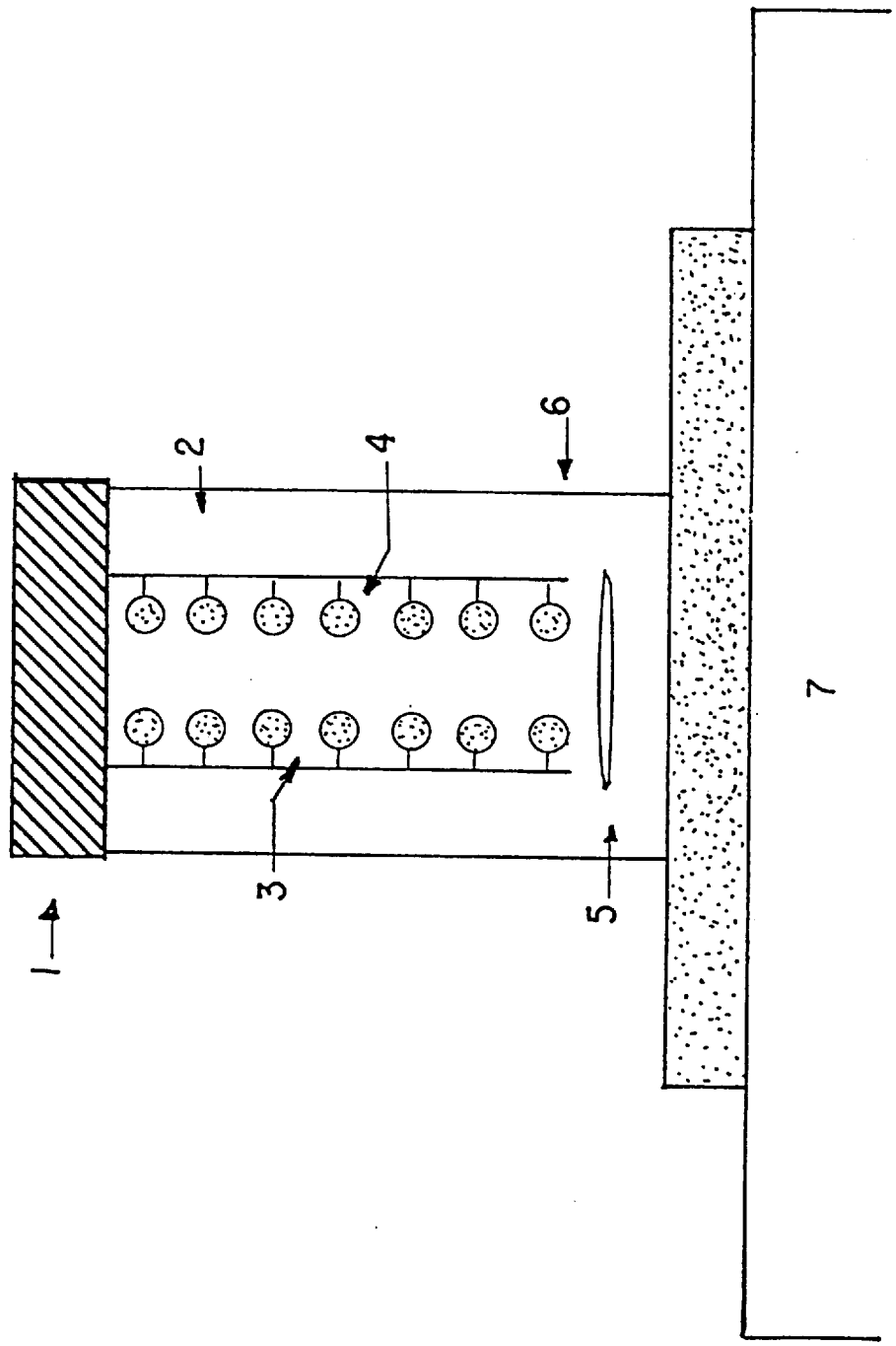

FIG. 4: Schematic of a peptide generating and screening apparatus in which selective fluid communication is achieved by immobilizing both protease and macromolecular sink molecules. 1=cap, 2=protein and/or peptides, 3=immobilized enzyme, 4=immobilized macromolecular sink, 5=stir bar, 6=reservoir, 7=magnetic stirrer.

In this technique a substrate (i.e., peptides or protein) mixture is placed in a holding reservoir (of any practical volume). The macromolecular sink (receptor) is attached to glass or sepharose beads which have been immobilized onto a rigid support. Similarly, the enzyme is attached to glass or sepharose beads which have been immobilized onto a separate rigid substrate. The macromolecular matrix and the enzyme matrix are immersed into the substrate mixture and spatially separated from each other. Low molecular weight peptides generated as a consequence of interaction between the immobilized enzyme and the protein, peptide mixture interact with the immobilized macromolecular sink. After a suitable period of time, the rigid macromolecular sink support is removed and evaluated for peptides which have bound to the macromolecule. The binding chamber is sealed with a cap to ensure sterility of the system, and the contents of the reservoir are stirred to ensure adequate mixing of the protein, peptide solution.

Figure 5:
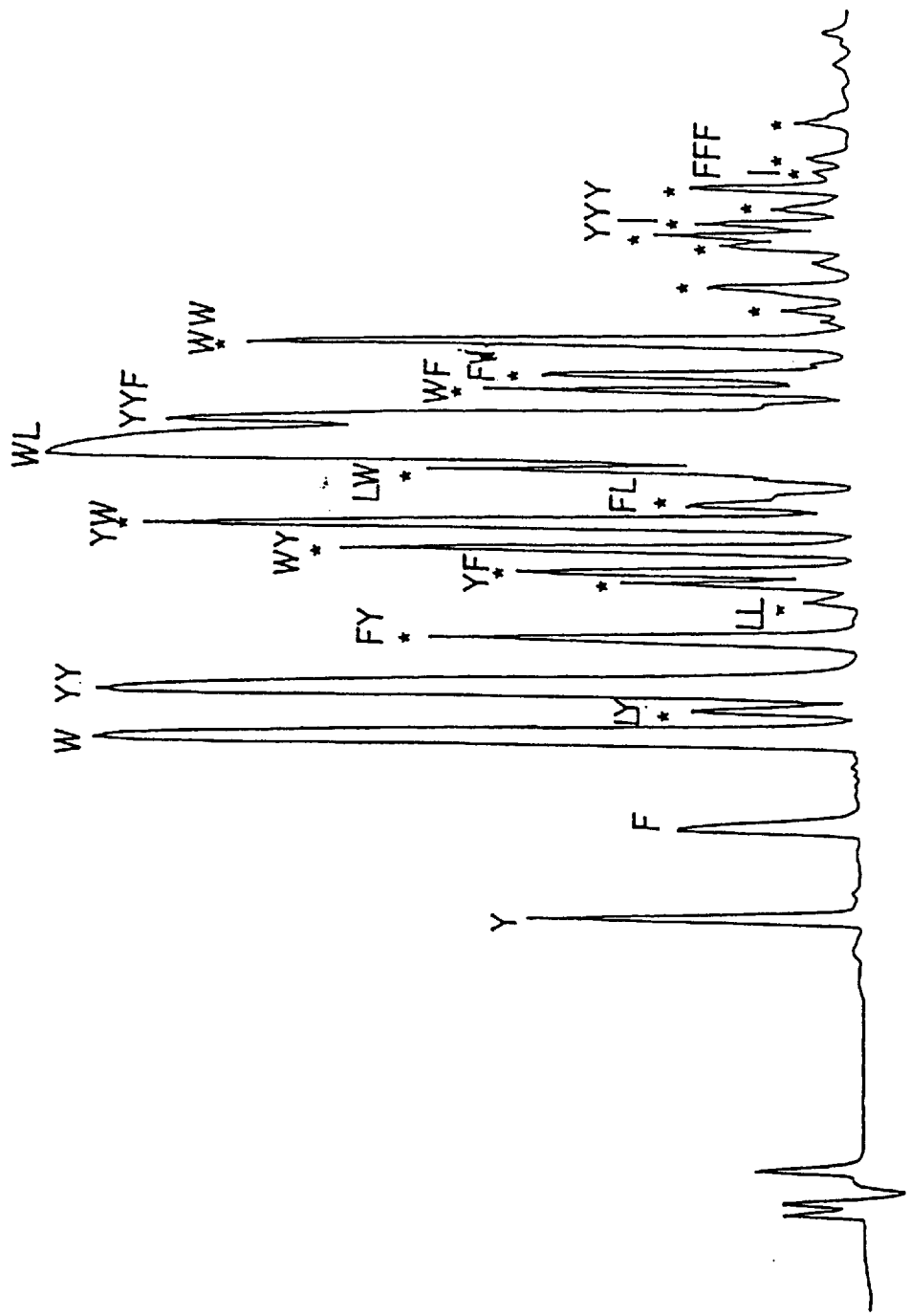

FIG. 5: A chromatogram ($C_{18}$) of the mixture of peptides resulting from digestion of WL and YYF with thermolysin for 24 hours. Scrambled peptides—peptides other than starting material or cleavage products—are starred.

Figure 6:
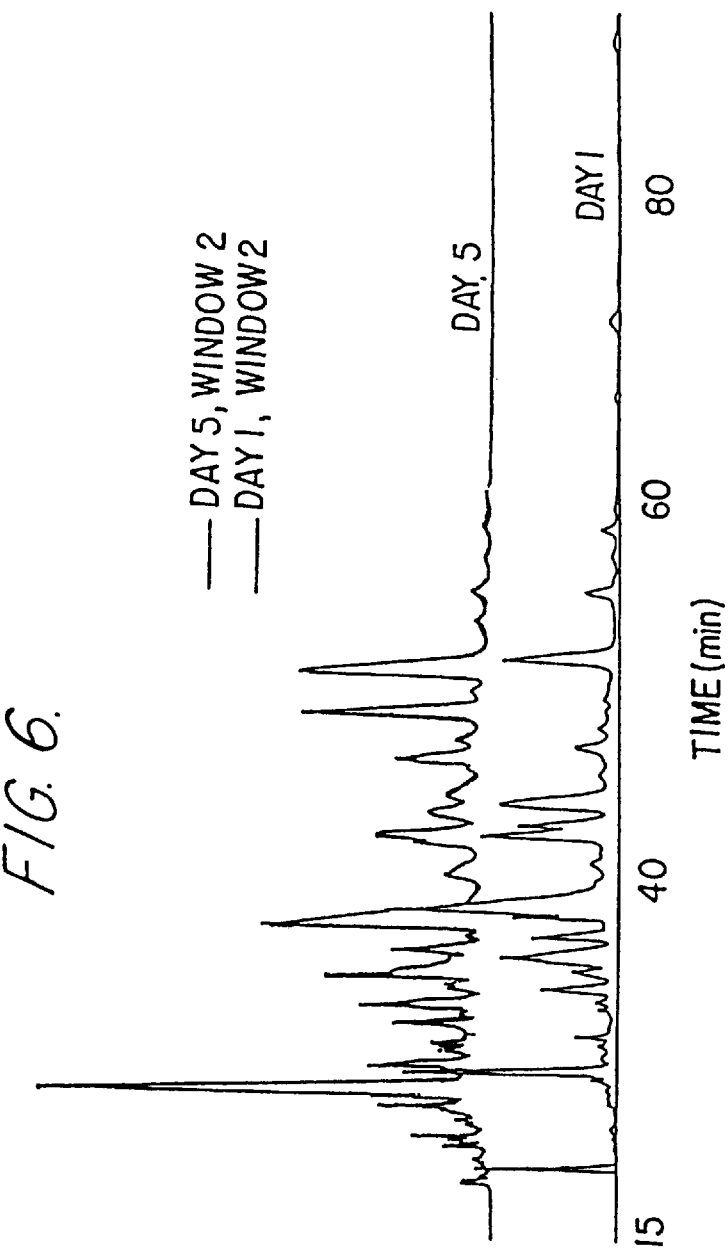

FIG. 6: Capillary electropherogram of peptide mixture at days 1 and 5 after digestion of BSA with bromelain, subtilisin BPN, and thermolysin.

Figure 7:
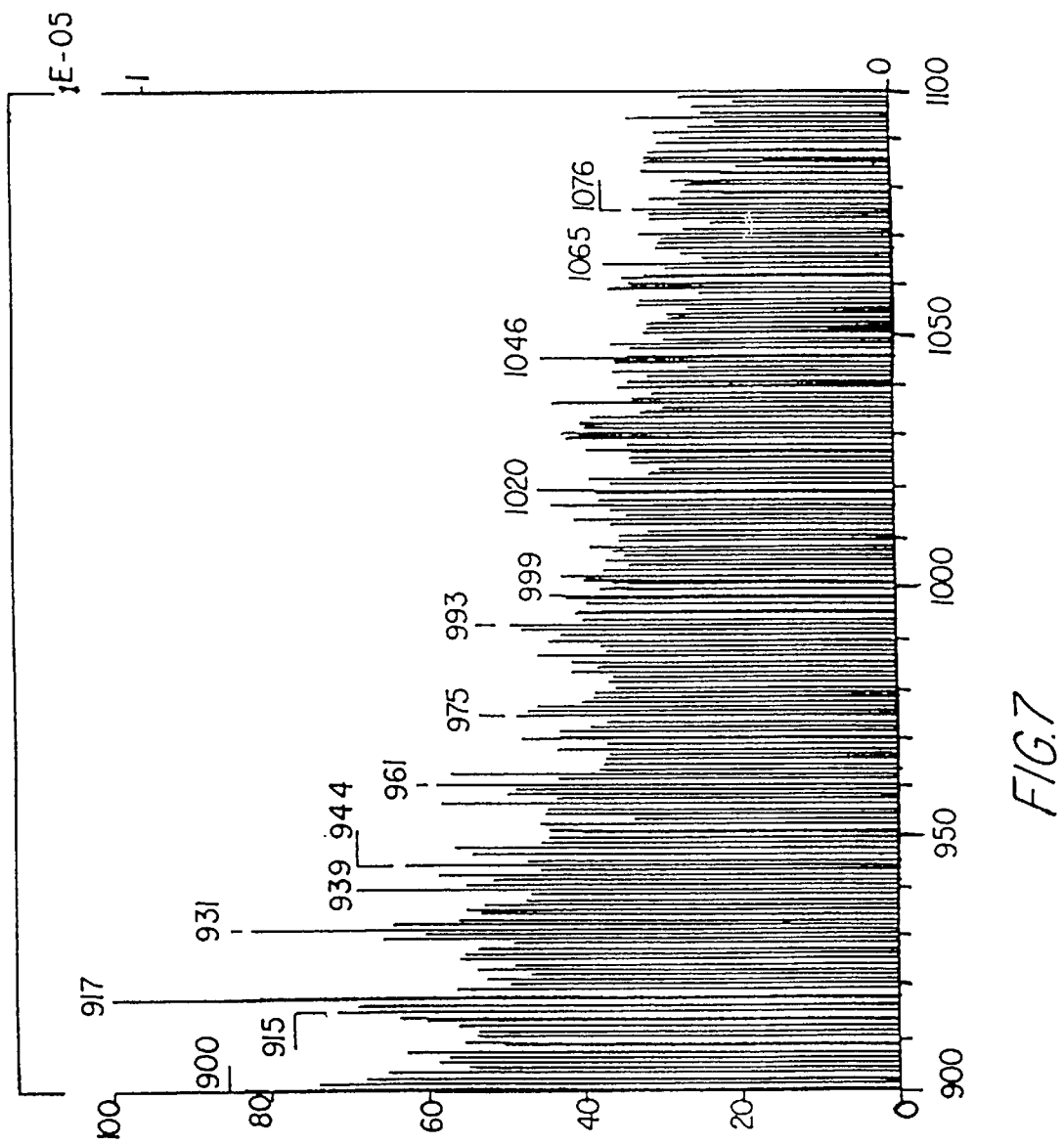

FIG. 7: Fast Atom Bombardment Mass Spectrogram of the same peptide mixture at day 5, with species in the 900–1100 dalton range shown. Note that the average mass of an amino acid is about 100 daltons.

Figure 8B:
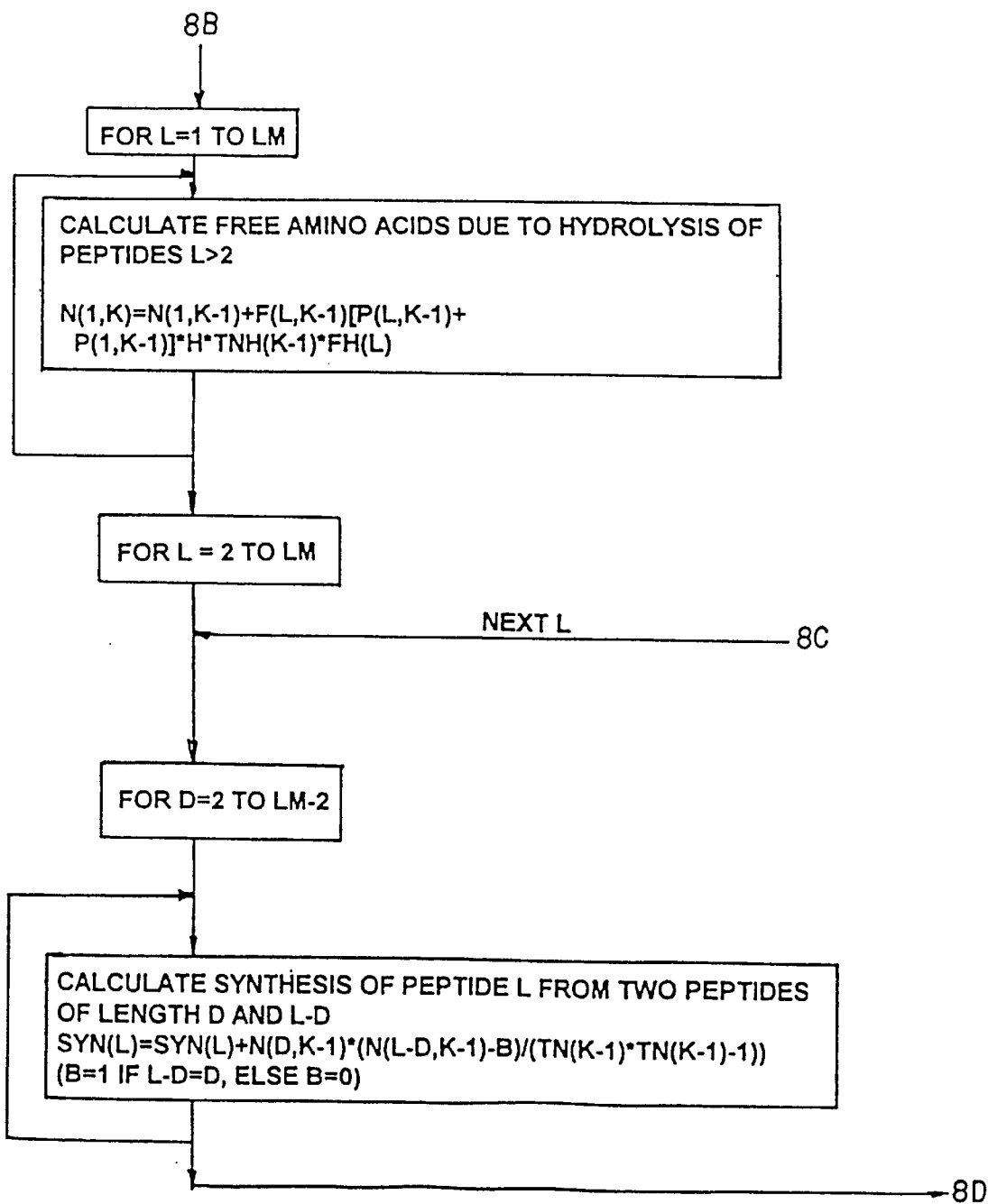

FIG. 8: Flow chart of computer program to predict number and length of peptides in scrambling reaction.

Figure 9A:
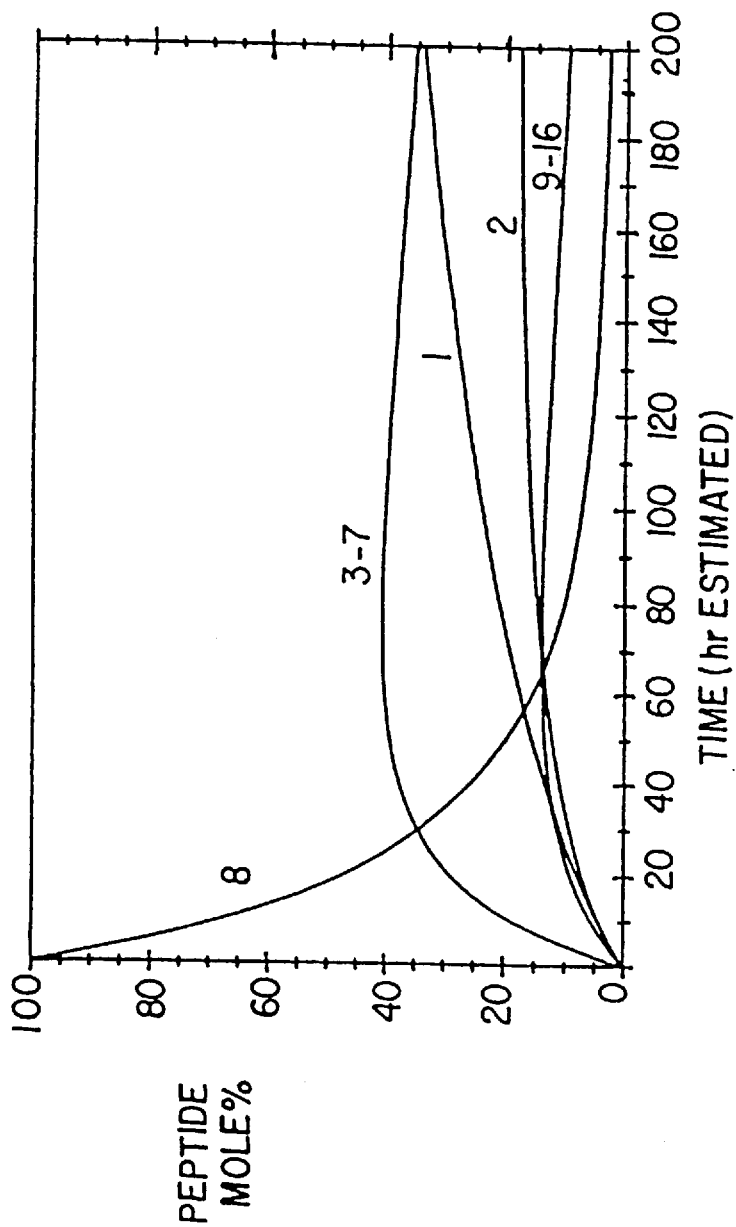
Figure 9B:
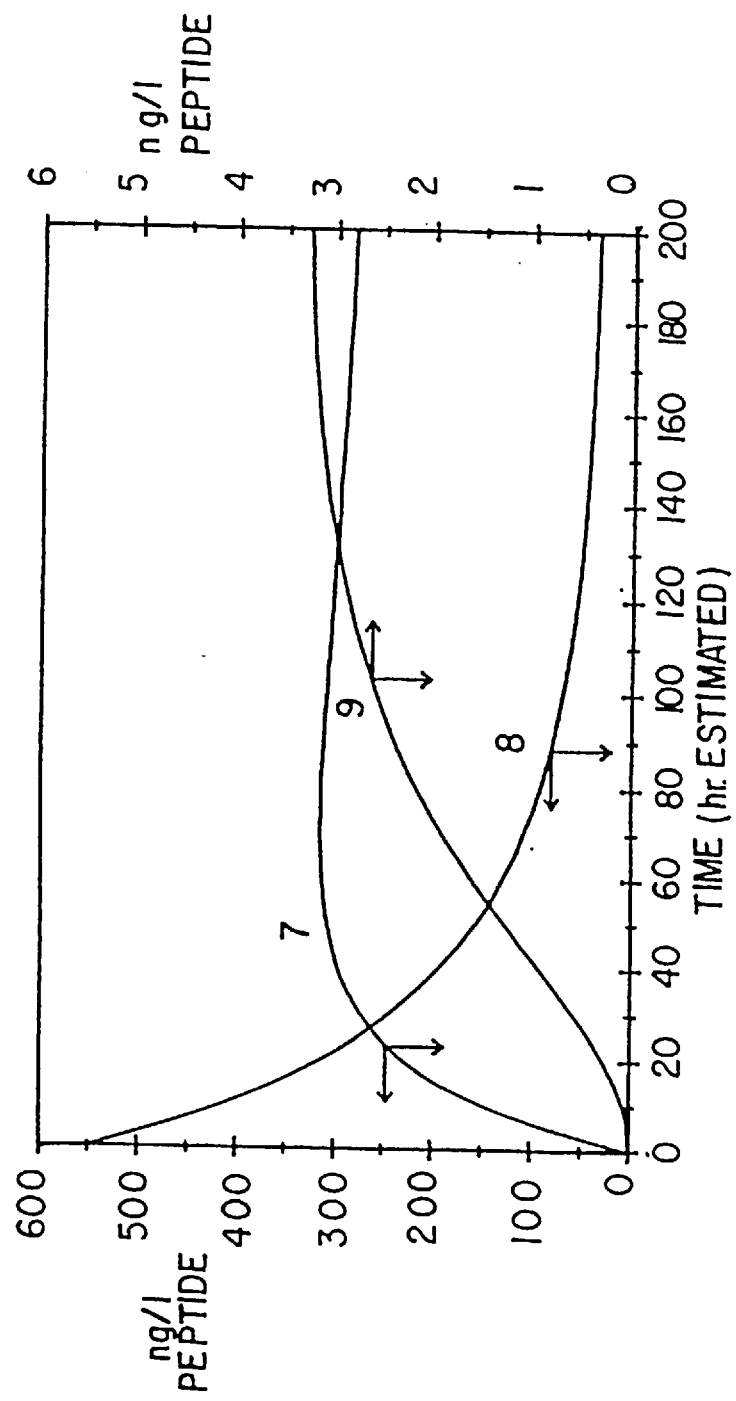

FIG. 9: Results predicted by computer model.

Figure 10:
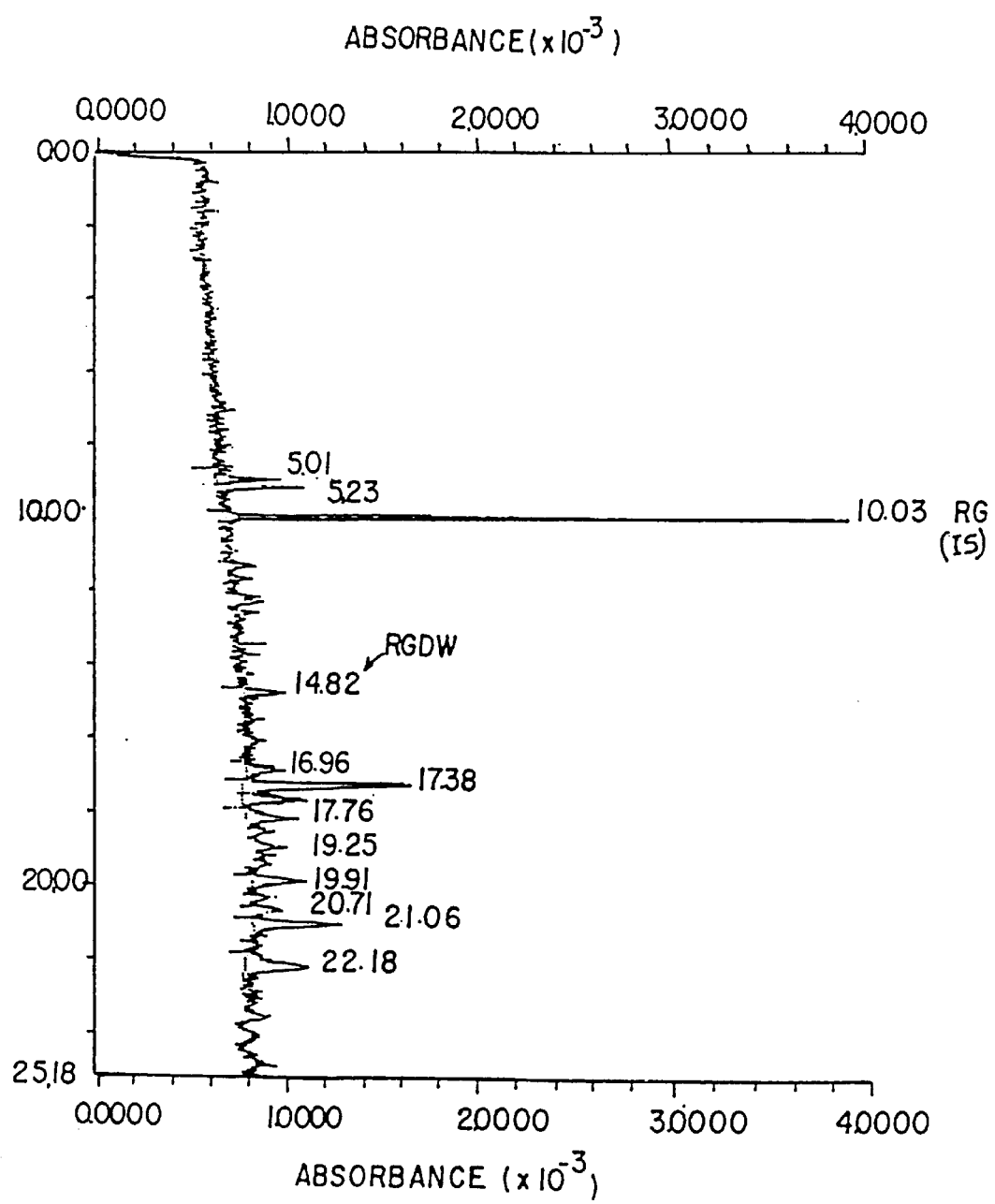

FIG. 10: is a capillary electropherogram of the RGDW fraction collected by reverse phase HPLC from the peptides bound to $G_pII_bIII_a$ (fibrinogen receptor).

Figure 11:
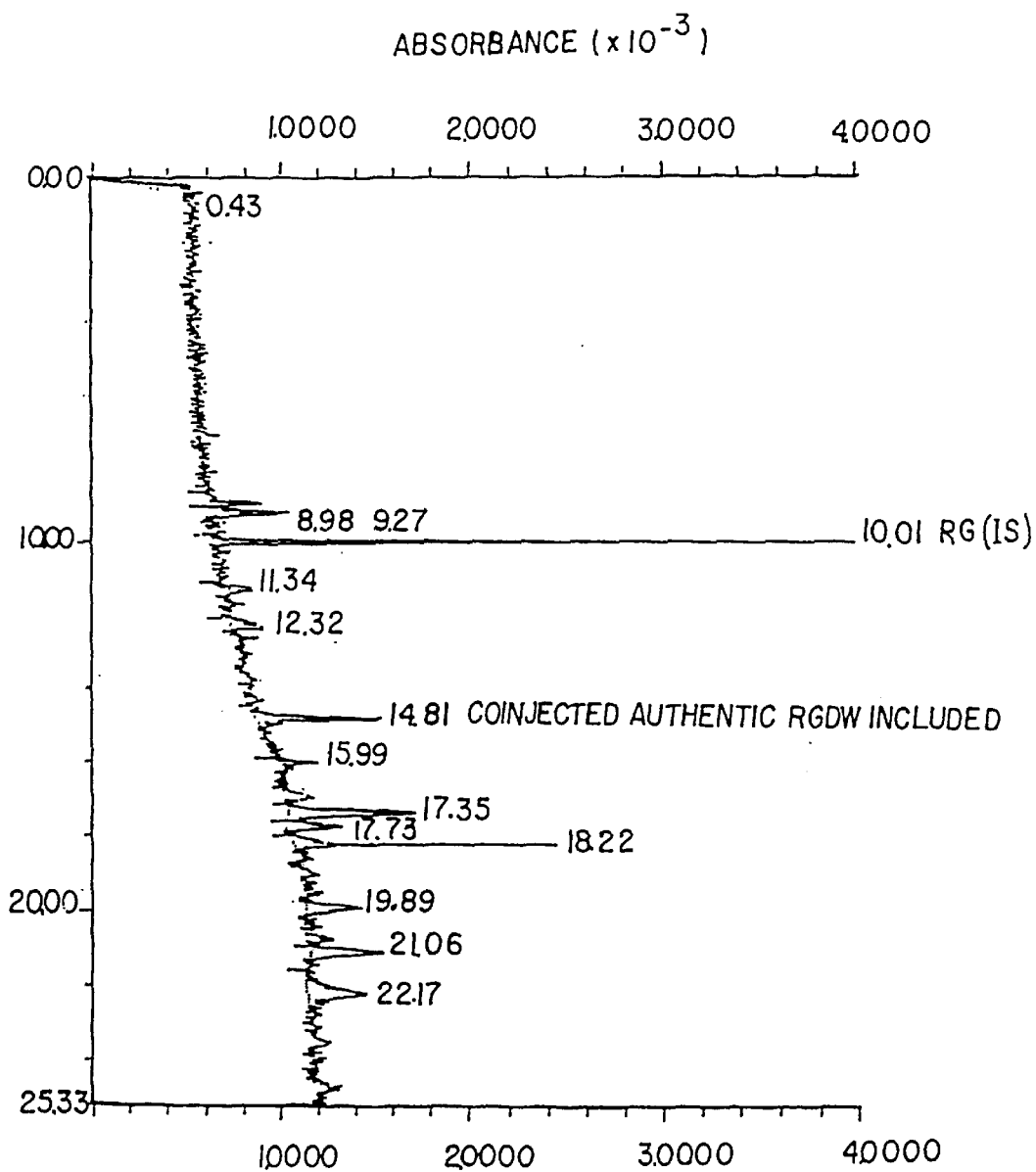

FIG. 11: shows the capillary electropherogram of the same fraction spiked with an RGDW standard.

Figure 12:
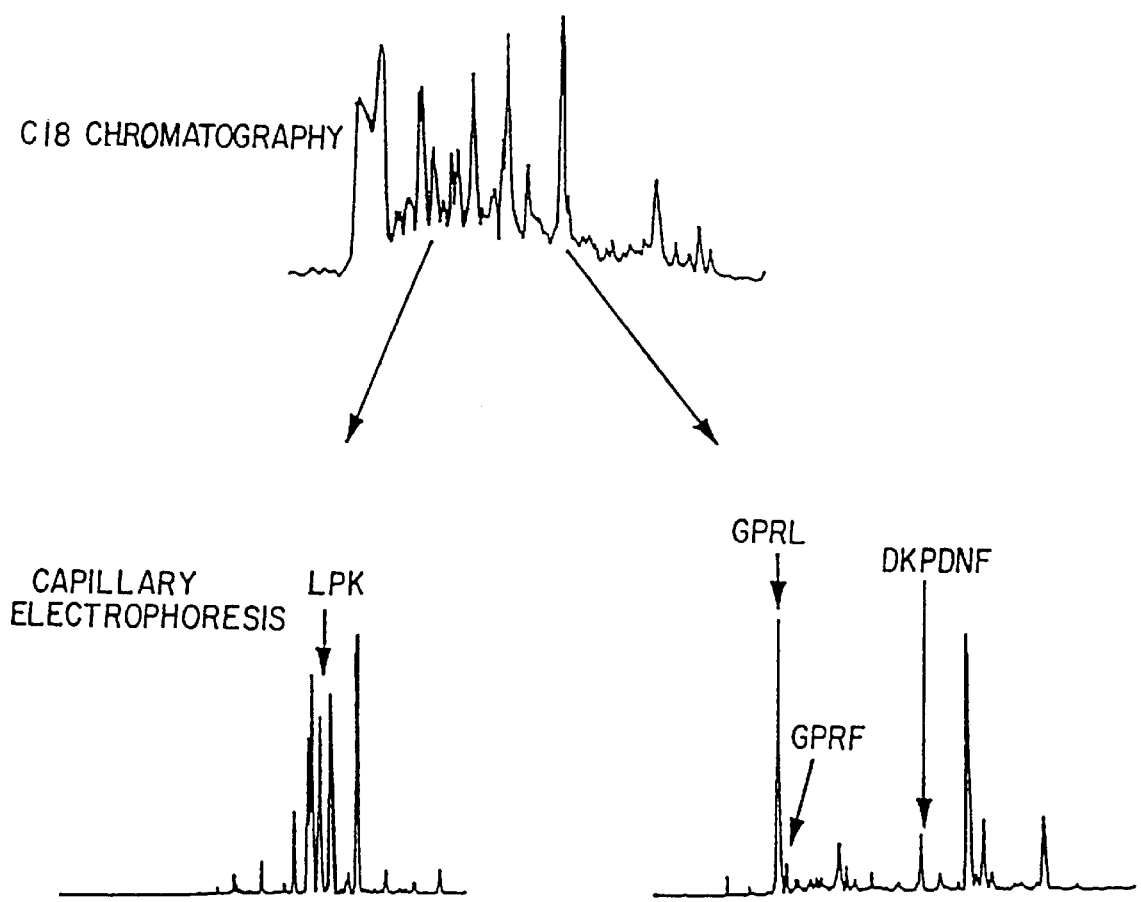

FIG. 12: depicts various analyses of fibrinogen binding peptides.

Figure 13:
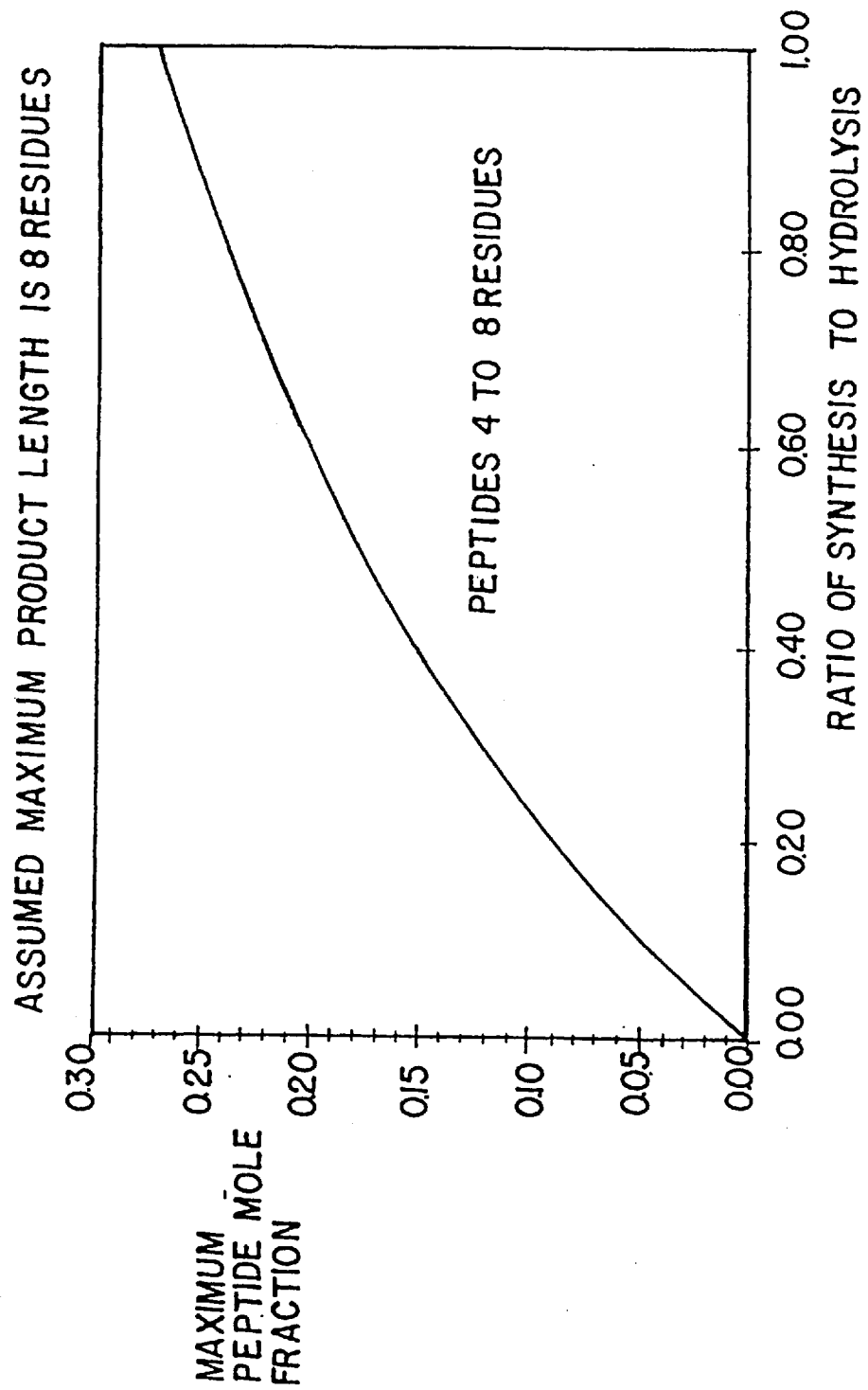

FIG. 13: is a graph of maximum mole percent of peptides 4 to 8 residues as a function of the ratio of the synthesis rate to the hydrolysis rate.

Figure 14:
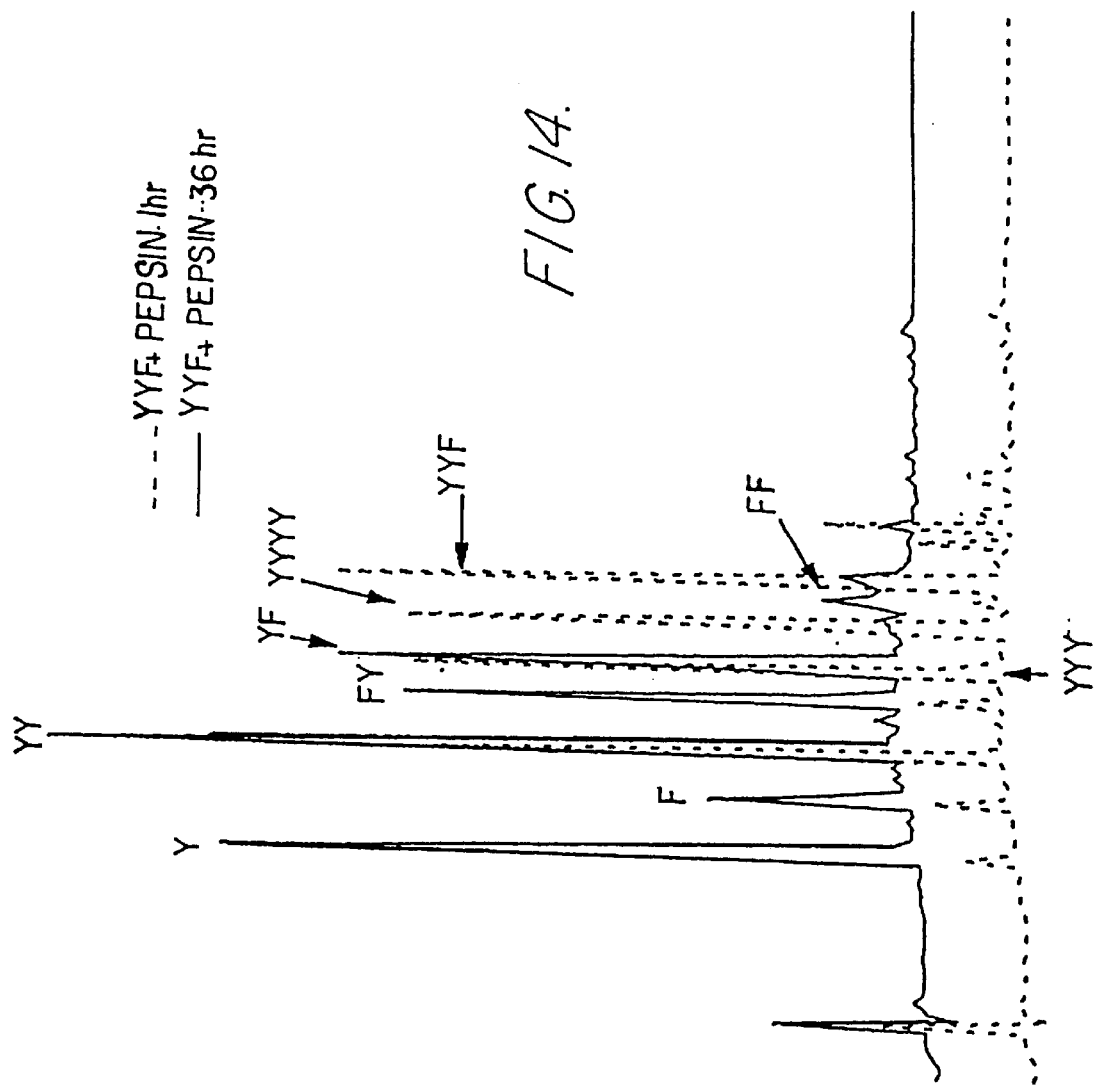

FIG. 14: shows the peptide profile of a YYF/pepsin scrambling system at one and 36 hours after initiation of the reaction.

Figure 15:
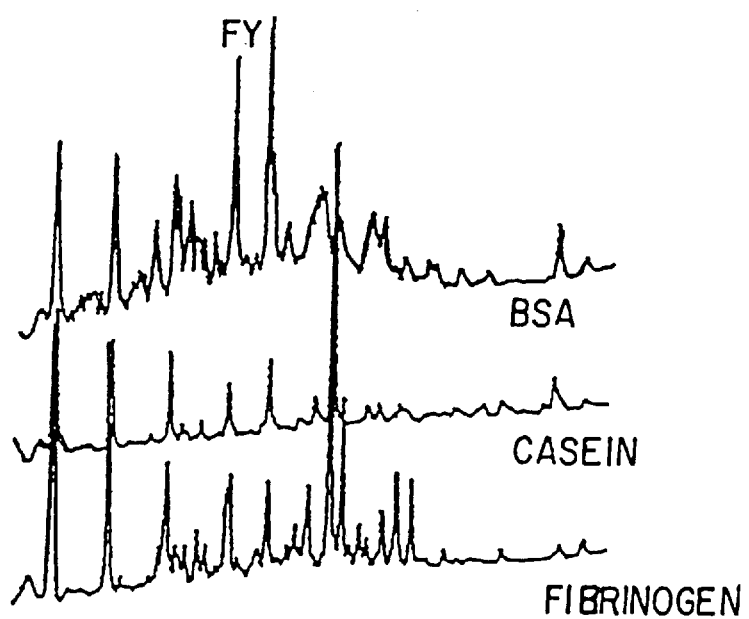

FIG. 15: shows the elution profile of peptides bound by BSA, casein and fibrinogen, obtained by screening of an FY/pepsin scrambling system.

DESCRIPTION OF THE SPECIFIC EMBODIMENTS

A method is provided for synthesizing a population of peptides containing large numbers of peptides of varied sequence within a particular size range and for screening that population for the presence of one or more peptides which specifically bind to a particular macromolecule.

The method involves, in a preferred embodiment, a "scrambling" reaction which utilizes as starting material, one or more non-specific proteases and a mixture of size-selected peptides, isolated by gel permeation chromatography of a digest of an inexpensive natural protein, such as casein, or a mixture of natural proteins. The "scrambling" reaction relies upon the fact that enzymes are catalysts and thus can facilitate reactions in either direction. For proteolytic enzymes, this means that proteolysis (degradation of peptides to smaller peptides and amino acids) and peptide synthesis (coupling of peptides and/or amino acids to form peptides) can be facilitated by the same enzyme.

The equilibrium position (synthesis versus degradation) is primarily determined by the concentration of amino acids and other peptide products. For an equilibrium position at which synthesis and degradation are balanced, peptides are continuously being randomly synthesized and randomly degraded, and thus true "scrambling", i.e. the generation of a multiplicity of peptides containing greatly varied combinations of amino acids, occurs. Such a multiplicity of peptides may be generated by rearranging amino acids within or among peptides, and/or by digesting protein to yield peptides, followed by addition of amino acids to such peptides. Proteolytic enzymes may be employed to carry out the rearrangement or digestion and addition processes.

Initially, the scrambling zone will contain only the starting proteins, peptides and/or amino acids (collectively, the "starting peptide mixture"). As the scrambling progresses, two other classes of molecules will appear: peptide and amino acid fragments of the added proteins and peptides; and scrambled peptides. For the purpose of the appended claims, a "scrambled peptide" is one which cannot be obtained merely by hydrolysis of the starting peptide mixture; some addition must occur as well. Of course, all components of the scrambling zone—added proteins, peptides and amino acids; simple peptide and amino acid fragments; and scrambled peptides—which are able to pass into the trapping zone will be screened for activity.

The scrambling reaction should generate a plurality of scrambled peptides. Preferably, the scrambling reaction produces at least $10^3$, more preferably at least $10^6$, different scrambled peptides. Desirably, the system evolves so that the scrambled peptides are at least 99%, more desirably at least 99.9%, of the total number of different peptides.

It should be understood that the term "random", as used above, does not necessarily mean that all possible peptides are equiprobable; in the starting peptides, some bonds may be more labile than others; the starting mixture may contain only a selected subset of the possible amino acids; the proportions of the amino acids present may be unusual; and the starting mixture may be biased by the incorporation of selected peptides of predetermined sequence.

These processes can result in a large number, even up to the theoretical maximum number, of unique peptides being produced for a peptide of any given size. For example, for an average peptide size of eight amino acids the theoretical maximum number of distinct peptides produced would be up to about $20^8$ or about $2.56 \times 10^{10}$. Each of these peptides would be expected to have its own unique spatial and thermodynamic binding properties and, thus, its own unique capacity to bind to a particular target macromolecule. In comparison, the human antibody repertoire, long considered to represent the apex of binding diversity, produces a maximum of about $10^9$ unique spatial thermodynamic binding states. It should be recognized, however, that the number of distinct peptides may be less than this maximum theoretical number. This is due to the possible existence of local energy minima around which a steady state condition might develop, preventing a true global equilibrium from occurring. Considerable variation, however, would still be expected in such a system. Such variation need not necessarily approach the maximum theoretical number to be able to result in the production of useful specific binding peptides.

The method further involves producing and selecting analyzable quantities of one or more peptides which specifically bind to a particular macromolecule. This is done by favoring the net synthesis of such peptides by removing them from the scrambling system, thus shifting the equilibrium. The peptides are removed from the system by specific binding to a specific macromolecule "trap" which may be physically separated from the "scrambling" mixture by a semi-permeable barrier which allows passage of peptides up to a particular size without allowing passage of macromolecules, including proteases. By selectively removing a particular peptide product from the "scrambling" reaction at equilibrium, and thus preventing it from being degraded, the net synthesis of that peptide can be achieved without requiring the impracticable net synthesis of equivalent quantities of each of the other twenty-five billion (or more) peptides.

Thus, the invention allows the generation and screening of a population of peptides for the presence of peptides which specifically bind a particular macromolecule, and further allows the favored net synthesis of analyzable quantities of such peptides. By using as the "trap" a macromolecule for which binding of the peptide is desired, e.g., classical biological receptors, specific immunoglobulins, structural proteins, etc., peptides which are useful may thus be selected.

These specifically binding peptides can then be separated from the macromolecule and each other by standard procedures and identified by amino acid sequencing.

Once this identification has been made, this fully enables one skilled in the art to produce unlimited quantities of the specifically bound peptide by standard synthetic means. Thus the methods of the invention enable both the production of specifically bound peptides by the method of the invention, and the production of large quantities of peptides having amino acid sequences identical to specifically bound peptides produced by the methods of the invention.

The method of the invention comprises the protease-catalyzed "scrambling" of peptides to yield a multiplicity of peptides comprising massive numbers of unique spatial and thermodynamic properties, coupled with net synthesis of peptides which bind to particular macromolecules and identification of said peptides according to their amino acid sequence.

Starting Mixture

The peptides of the starting mixture do not have a fixed upper limit to their length. However, several considerations lead us to prefer a mixture in which the peptides have a mean length in the range of from about 2 amino acids (a.a.) to about 15 a.a. in size. First, this range encompasses most bioactive peptides. Secondly, the number of possible peptides increases exponentially with the length of the peptide, thus, as peptide length increases, the ability of the scrambling system to sample all possibilities diminishes.

The mixture may further contain amino acids in free form, however, these amino acids do not participate as readily in the scrambling reactions as do the oligopeptides.

Those skilled in the art will recognize that the starting peptides may be derived from a variety of sources. Sources of the peptides would include proteolytic digests of naturally occurring proteins as well as chemically synthesized peptides. Most preferred is the use of peptides which have been generated by proteolytic digestion of an inexpensive protein, such as casein. The most preferred size range for starting peptides is from about 7 a.a. to about 10 a.a. Peptides having the desired length may be obtained by fractionation of the aforementioned digest. Fractionation may be by any technique capable of separating oligopeptides according to size, including but not limited to gel-permeation chromatography. The method chosen is preferably capable of resolving peptides having a three amino acid difference in length.

Preferably, the starting mixture will contain all, or nearly all, of the 20 naturally-occurring amino acids. However, it should be noted that many useful peptides do not contain all 20 of the naturally occurring aminio acids, and it is possible to provide a starting mixture in which only selected amino acids are provided, or in which the proportions of the amino acids are biased in some way. For example, if it is desired to improve upon the activity of a known oligopeptide of a defined amino acid sequence, it may be desirable to limit the mixture to, or bias it toward, amino acids similar to those found in the known oligopeptide. Amino acids may be favored or disfavored on the basis of their size, hydrophilicity, charge, etc., or on the basis of their reactivity in the scrambling reaction. The bias may be introduced by use of oligopeptides (natural or synthetic) providing the favored amino acids, and/or by inclusion of free amino acids.

The starting mixture may also be "spiked" with one or more peptides ("lead" molecules) (see, e.g., Table 6) having the desired activity, or a related activity. This lead peptide preferably has an affinity (Kd) for the target, or for a related molecule, of at least $10^{-4}$ moles, more preferably $10^{-5}$, and still more preferably $10^{-6}$. For example, RGDW [SEQ ID NO=1] has an affinity of $5 \times 10^{-6}$ for fibrinogen receptor. The presence of this "spike" peptide will bias the scrambling system toward exploring mutations of this "spike" peptide, with the degree of bias being dependent on the spike concentration. The range of variation possible is dependent on the composition of the spike peptide and of the secondary peptides present. Among the possibilities are the following:

1. The starting mixture contains only the lead molecule and, as a source of variation, secondary molecules selected from the group consisting of the free amino acids of which the lead molecule is composed and other oligopeptides composed only of amino acids found in the lead molecule.
2. The starting mixture also provides some but not all of the amino acids (free or within an oligopeptide) which are not found in the lead molecule.
3. The starting mixture contains the full complement of amino acids.

When a lead peptide is employed, it is preferably introduced at a high concentration, such as 1 mM to 100 mM. It is preferably at least about 10%, more preferably at least about 25% still more preferably at least about 50%, of the total amino acid-containing substrate of the starting mixture.

Instead of spiking the mixture with a lead molecule, one may spike it with a set of peptides which collectively provide the amino acids found in a known biomolecule. (The peptides may be subsequences of the biomolecule, but this is not required.) This will favor the synthesis of analogues of the biomolecule.

The present invention is not limited to the use of the twenty directly encoded amino acids. Other amino acids, such as hydroxyproline, norleucine, and so on, may be provided in the starting mixture either in free form or as residues of an oligopeptide. These amino acids may be, but need not be, amino acids which occur in biological systems.

In one embodiment, the starting mixture of peptides is obtained by digestion of protein. For example, an inexpensive protein, such as casein, bovine serum albumin, ovalbumin, lactalbumin, bovine kidney acetone powder, intestinal acetone powder, hemoglobin, edestin, chicken egg whites, cucurbit seed globulin, etc., or mixtures thereof is digested with a suitable concentration, such as approximately $10^{-6}\underline{M}$, with approximately 0.5% weight percent of a nonspecific protease or combination thereof, such as papain, pronase, or subtilisin. At ambient temperature (25° C.) the digestion requires about two hours. The digested material is fractionated by gel-permeation chromatography on a polyacrylamide matrix (e.g., Bio-Rad, Bio-GelM). Fractions containing peptides of about 7–12 a.a. are collected, lyophilized and reconstituted at a concentration of about $10^{-2}\underline{M}$ for use in the scrambling reaction. Alternatively, a similar, and adequate, starting peptide distribution may be obtained by carrying out the digestion directly in the reaction chamber 1 in FIG. 1. Thus, about 3 L of a solution of $10^{-2}\underline{M}$ of the same inexpensive proteins or mixtures thereof are digested with approximately 0.50% weight percent of a nonspecific protease or combination thereof. The desired molecular weight distribution of small peptides having 7–12 a.a. is adjusted by either adding more protein, which will increase the average peptide length (i.e. higher concentration of a.a. and increased synthesis), or diluting the peptide mixture to decrease the peptide chain length (i.e. increased hydrolysis of existing peptides). The actual peptide size distribution is monitored by removing an aliquot of the reaction mixture from valve 2, FIG. 1 and subjecting it to gel permeation chromatography using polyacrylamide gels. For both methods of making starting peptides, the equilibrium mixture may be further supplemented with an amino acid and/or small peptide whose inclusion in a given binding peptide is considered particularly desirable, or whose rate of reaction in the scrambling reaction is particularly low.

The starting peptides may be present at a concentration from about $10^{-1}\underline{M}$ to about $10^{-6}\underline{M}$, more usually at a concentration from about $10^{-1}\underline{M}$ to about $10^{-4}M$. The most preferred concentration of starting peptides is about $10^{-1}\underline{M}$ (100 mM) to $10^{-3}\underline{M}$ (1 mM). It should be understood that not all reagents useful in the present invention will be wholly soluble under all circumstances. Therefore, molarity, for purposes of the present invention, should be construed to mean only the number of moles of material added per liter of solution, and not the number of moles actually solvated per liter of solution.

Instead of, or in addition to, peptides, the starting mixture may contain proteins, as the proteins will be hydrolyzed in situ to obtain peptides.

Scrambling Reagents

The starting peptides are "scrambled" by balanced synthesis and degradation catalyzed by proteolytic enzymes. One or more proteolytic enzymes may be added to the solution of starting peptides as scrambling proceeds. The preferred proteolytic system for the "scrambling" reaction is a combination of distinct, relatively nonspecific proteases. Most preferred is the use, singly or in combination, of papain, pepsin, bromelain, thermolysin, subtilisin, trypsin and/or chymotrypsin. The total protease final concentration is typically 100–500 µM, depending on solubility. However, it will be understood that these numbers do not reflect hard and fast limits. Rather, the total concentration of proteases must be sufficient to achieve the desired degree and rate of scrambling.

Alternatively, scrambling may be accomplished by chemical, rather than by enzymatic means. Any catalyst, whether enzymatic or not, effectively lowers the energy level of the transition state of a reaction, thus allowing it to proceed more readily in either direction. Scrambling may therefore be achieved with other catalysts known to cleave the amide bond, e.g., CNBr, mineral acids such as HCl, and metal chelates, by choosing suitable solvents and reactant concentrations. See Collman, et al., *J. Org. Chem.,* 9(5), 1183 (1970).

The Scrambling Reaction

The balance between synthesis and hydrolysis is a function of the concentrations of protein and peptides present. When protein levels are high, hydrolysis is favored. As peptide concentration increases and protein concentration decreases as a result of protein hydrolysis, the synthesis rate will increase until an equilibrium is reached between synthesis and degradation.

When the starting substrate is a protein such as casein, it is preferably added in high (more preferably, essentially saturating) concentrations. This will result in the rapid hydrolysis of the protein, and subsequently in high peptide (hydrolysate) concentrations, which in turn will favor increased synthesis.

Alternatively, a starting peptide mixture may be prepared either by direct synthesis of the peptides, or by first digesting a protein such as casein, and then concentrating the hydrolysate, leaving any still extant protein behind. This hydrolysate may then be used as the starting mixture for the scrambling system, and added to the reaction vessel in high (more preferably, essentially saturating) concentrations.

While amino acids may be included in the starting mixture, it is more difficult to couple two amino acids together, or an amino acid to a peptide, than to condense two peptides together.

The scrambling system should exhibit a substantial level of synthesis. Preferably the scrambling reaction, at least after equilibration, exhibits a synthesis rate which is more than 0.05% of the hydrolysis rate, more preferably greater than 0.5%, still more preferably greater 5%, and most preferably greater than 25%.

The relative rates of synthesis and hydrolysis may be inferred from the size profile of peptides obtained in the course of scrambling, with the appearance of larger peptides than those of the starting mixture being indicative of a relatively high rate of synthesis. See, e.g., FIG. 14, showing the evolution of a YYF/pepsin scrambling system. After 36 hours, one of the major components was the tetrapeptide YYYY [SEQ ID NO:2]. This tetrapeptide is not a simple fragment of YYF or pepsin, and presumably evolved by release of Y or YY from YYF and subsequent recombination of these Ys and YYs to form the tetrapeptide YYYY. Similarly, in Example 5, the hexapeptide product DKPDNF [SEQ ID NO:3] is not a simple fragment of BSA.

Preferably, at least 10% of the peptides obtained by scrambling are larger than the peptides of the starting mixture.

In one embodiment, about 3 L of a solution of $10^{-2}\underline{M}$ peptide fragments of 7–12 a.a. in size is added to the reaction chamber (FIG. 1) via the micro-filtration apparatus (to maintain sterility). This is followed by a mixture of *S. griseus* protease, papain, and subtilisin at about 0.5 g per 100 g of peptide substrate. The scrambling reaction is incubated with stirring at about 25° C. Alternately, this same point is reached by direct digestion of inexpensive starting proteins. To assess the state of the desired global equilibrium, and thus the amount of scrambling, any of several techniques given below are employed. In both cases, the peptide length is periodically monitored, e.g., by removing an aliquot of the reaction mixture from the reaction chamber and subjecting it to gel permeation chromatography using polyacrylamide gels, or other resin materials providing suitable resolution.

Peptides which are too small may have inadequate specificity or affinity for the target, while those which are too large have increased production costs and possible bioavailability problems. If the peptide size distribution is unsatisfactory, it may be adjusted. Adding proteins, or peptides of greater length than the current mean length, will increase the rate of degradation (as a result of the law of mass action), but the system will reach a steady state at which the mean peptide length is intermediate between the original mean length and the mean length of the added peptides. Cosolvents, such as glycerol (16% V/V), 1,4-butanediol (40–60%), and acetonitrile (10–15%), may increase the rate of synthesis (reverse hydrolysis), which will, all else being equal, increase the mean peptide length.

Adding amino acids, or peptides of a length smaller than the current mean length, will increase the rate of synthesis, but the new steady state mean peptide length will be lower than the previous one. (Note, however, that free amino acids do not appear to be readily incorporated, but it is possible that this problem could be overcome with the aid of cosolvents such as glycerol or dimethyl sulfoxide.) Diluting the mixture (with a compatible diluent) will also tend to lower the mean peptide size.

The rate of scrambling may also be adjusted. If the mean peptide length is satisfactory, but the degree of scrambling is inadequate, the temperature or the enzyme concentration may be increased, or peptides of the same mean length may be added. If the rate of scrambling is too high, the temperature or the enzyme concentration may be reduced (e.g., by diluting the mixture and then adding peptide).

Target Molecules

In one embodiment, the target is a macromolecule. There is no theoretical limitation on the type of macromolecule or macromolecule complex which may be used as a trap (target). The use of biological and biochemical techniques has allowed the identification of numerous biomolecules whose modulation could alter a pathological state. These molecules and molecular complexes include, but are not limited to receptors, specific antibody classes, structural proteins RNA, DNA, polysaccharides and enzymes.

The term "receptor" is defined, for purposes of the appended claims, as any cell-associated macromolecule or macromolecular complex which, when bound by a ligand, alters the biology of the cell, or a synthetic cognate or analogue of such a molecule. Examples of classical receptors which have been identified and cloned include the dopamine receptors (D1 and D2), opiate receptors, benzodiazepine receptors, adrenergic receptors (alpha-1, 2 and beta-1, 2), cholinergic (muscarinic) receptor, calcium, sodium or potassium channels, glucocorticoid receptor, fibrinogen receptor and fibronectin receptor. Further examples are receptors for insulin, estrogen, LDH, progesterone, inositol triphosphate, and seratonin, among others.

Specific antibody classes include those involved in organ transplant rejection and autoimmune diseases such as rheumatoid arthritis, multiple sclerosis, Graves ophthalmopathy, psoriasis, insulin-dependent diabetes and systemic lupus erythematosus.

Structural proteins and enzymes include those associated with pathological viruses or bacteria such as the common cold (rhinovirus), hepatitis A, influenza, respiratory syncytial disease virus, HIV and cancer inducing viruses (e.g., HPV) Specific examples include the rhinovirus capsid protein, the reovirus hemagglutinin receptor and HIV gp120 protein. Further examples are dihydrofolate reductase and penicillinase, among others.

Nonviral structural proteins and enzymes include sickle cell hemoglobin and specific protein kinases associated with neoplasia. Further examples are collagenase inhibitors, HMG-CoA, reductase inhibitors, angiotensin converting enzyme inhibitors, renin inhibitors and thymidylate synthetase inhibitors.

In principle each macromolecule or macromolecular complex presents a unique surface recognizable by a distinct set of spatial and thermodynamic properties and, thus, any macromolecule or macromolecular complex is theoretically capable of acting as a "trap."

A macromolecular trap may be a molecule which occurs in nature as a macromolecule, or one whose size has been increased to a macromolecular range by conjugation to a carrier substance. For the purpose of the present invention, the term macromolecule applies to a molecule having a molecular weight of at least about 15,000 daltons.

It is not necessary that the target be a macromolecule, provided that it can be modified as contemplated herein for use as a trap without changing conformation so much that peptides which bind the immobilized target do not bind the target in soluble form. The target may be a non-macromolecular moiety of a macromolecule of interest. For example, it may be a peptide fragment of a protein, or an oligosaccharide fragment of a carbohydrate. Of course, the fragment should have essentially the same conformation and binding characteristics which it did as a moiety of its parental macromolecule.

The concentration of macromolecule to be used as a trap is preferably within the range from about $10^{-10}\underline{M}$ to about $10^{-3}\underline{M}$. In a preferred embodiment the macromolecule concentration is from about $10^{-7}\underline{M}$ to about $10^{-5}\underline{M}$. Specific binding of the macromolecule by the peptide is defined as binding wherein the association constant is from about $10^4$ to about $10^{13}$ per mole. Peptides having affinities in this range are known as specific binding peptides. Most preferred are peptides with a binding affinity of at least about $10^5$ per mole, and which may cause a modulation of the activity of the bound protein.

Trapping of High Affinity Peptides

Selective net synthesis of peptides with a high binding affinity for a particular target (e.g., macromolecule) is achieved by removing such peptides from the "scrambling" cycle by allowing them to bind to a particular macromolecule "trap", and then protecting them from further scrambling after binding. This may be achieved by separating the "trap" from the "scrambling" reaction, for example, by a semi-permeable membrane which allows the free passage of the peptides, but not of the macromolecule or the proteolytic enzymes (or other scrambling reagent (s)). The separation may be on the basis of size, charge or other characteristics of the peptides, the target, and the proteolytic enzymes. Of course, where the target is a macromolecule and the enzyme is likewise larger than the peptides of interest, this separation is conveniently performed on the basis of size.

It is also possible to physically immobilize the target in a trapping zone and the scrambling reagent(s) in a separate scrambling reaction zone, while permitting the peptides to circulate between the zones. High affinity peptides will accumulate on the target, and thus have a reduced probability of being in the scrambling reaction zone.

Selective net synthesis may also be achieved, though less efficiently, even when there is no separation of trap and scrambling reagents, merely by periodically removing the traps from the reaction chamber, eluting off the bound peptides into a collection means, and returning the processed traps to the reaction chamber.

The apparatus may rely solely on diffusional processes to expose the peptides to the target(s) and to the scrambling reagents, however pumping means may be employed to increase the circulation rate.

Those skilled in the art will recognize that many configurations may be employed to separate the macromolecule "trap" from the "scrambling" reaction, such as by means of a semipermeable barrier dividing the apparatus into scrambling and trapping compartments. The only limitation is that the configuration should allow free passage of the binding peptide while preventing transmigration of the macromolecule "trap" or of any of the proteases. In other words, the barrier should allow the peptides to be in fluid communication with a specific binding macromolecule or macromolecular complex while preventing other macromolecules or macromolecular complexes (e.g., proteases) from having such communication.

The barriers are typically those used in macromolecule dialysis, desalting, concentration or isolation, and are commonly characterized by selective permeability with a molecular weight cut-off of about 15 kDa or less. Preferred barrier materials included cellulose nitrate, cellulose acetate, regenerated cellulose, polyamide, and polycarbonate polymers prepared in sheets, tubes or hollow fibers and with a permeability cutoff from about 0.2 kDa to about 20 kDa. Most preferred is a semipermeable membrane with a permeability cutoff of about 1–3.5 kDa. (This corresponds to a peptide length of about 10–35 amino acids, depending on the amino acids in question.)

The spatial relationship between the semi-permeable barrier, the "scrambling" reaction, and the macromolecular "trap" may vary, but in every configuration the semi-permeable barrier will completely separate the proteolytic enzymes from the macromolecule "trap". In certain embodiments, the barrier may be used as a "bag" containing either the "scrambling" or "trap" components, or could serve as a "window" between two or more compartments containing the "scrambling" and "trap" components of the system.

The trap may be preincubated with a ligand molecule bound by the target. If so, the molecules generated by the scrambling reaction will have to displace the ligand from the target in order to be trapped. In this way, one may select for scrambled peptides having a higher affinity than the aforementioned ligand for the target. Desirably, the ligand is labeled in a manner that facilitates its later separation from the scrambling reaction-generated binding peptides.

The compartment containing the trap may also contain one or more chaotropic agents. The effect of such agents will be to make it more difficult for the scrambled peptides to bind to the receptor. This is a second way of selecting for higher affinity peptides. The apparatus used for the scrambling and selection process may contain more than one target, in series or in parallel. If targets are presented in series, it is possible to remove peptides that bind to a first target so that they are presented in substantially reduced concentration to the second target. Alternatively, peptides that successfully bind to a first target may be removed from the original trap compartment and then placed in a second trap compartment containing the second target, thereby selecting for binding to both a first and a second target. If targets are presented in parallel, one may screen simultaneously for binding to any of a plurality of targets.

In one embodiment, reaction chamber a (See FIG. 1) is brought to equilibrium as previously described. A mixture of all twenty $^3$H-labeled a.a. or small peptides containing these a.a. (5 mCi, 0.1 $\mu$m total concentration) are introduced into the reaction chamber and the system is allowed to distribute the labels over the peptide mixture. Approximately 10 mL of a buffered, $10^{-5}\underline{M}$ solution of the human platelet fibrinogen receptor (Marguerie; et al. *J. Biol, Chem.* 1979, 254(12), 5357) is added to the hollow fibers of one of the parallel binding chambers in the synthesis/trapping apparatus shown in FIG. 1. The total system is allowed sufficient time to reach its new equilibrium state (or steady state), or for that time necessary to produce specific binding peptides of interest.

After a given time, an aliquot of the solution from the hollow fibers, containing the platelet fibrinogen receptor and bound peptides, is removed and subjected to gel filtration chromatography to separate the receptor peptide complex from unbound, non-specific peptides present in the solution (the latter are returned to the reaction chamber). Separation of bound peptides from non-specific peptides is completed by washing the filtrate with phosphate buffer using conventional ultrafiltration equipment. This leaves a platelet fibrinogen receptor complexed to peptides whose affinities are greater than about $Ka=10^6$. The platelet fibrinogen receptor complex, thus isolated, is heat denatured (100° C. for one hour) to release the bound peptides. These peptides, having specificity for the fibrinogen receptor, are then separated from the denatured receptor by ultrafiltration.

The solution of unique binding peptides for the fibrinogen receptor binding site are fractionated using standard chromatographic methods in combination or separately, i.e. reversed phase HPLC, isoelectric focusing, adsorption chromatography, partition chromatography, ion exchange chromatography, capillary electrophoresis, etc. Detection of the peptides is made using a scintillation counter.

The individual peptides are then sequenced by standard peptide sequencing techniques, synthesized, and evaluated for antiplatelet activity by conventional procedures. Those peptides, or synthetic modifications thereof, expressing antiplatelet activity are drug candidates for critical care treatment of various cardiovascular diseases.

In another embodiment, we may obtain selective net synthesis and identification of peptides which bind to renin. A buffered solution of commercially available renin (10 mL, $10^{-3}\underline{M}$) is added to the hollow fibers of a second parallel binding chamber in the synthesis/trapping apparatus shown in FIG. 1, and the system allowed to incubate for a period of time necessary to produce high affinity peptides of interest. This analysis can be conducted at the same time as that of fibrinogen receptor, since any competition for a particular peptide (or peptide fragment used in the synthesis of a particular peptide) between the two macromolecular sinks may only lengthen the time to reach a new global equilibrium (or new steady state), not its final state. Procedures identical to those described for fibrinogen receptor concurrently identify peptides having high affinity for renin. Such peptides having binding specificity for renin, or synthetic modifications thereof, are potential candidates for inhibiting renin function and thus for the treatment of hypertension.

In a third embodiment we generate and screen selective net synthesis and identification of peptides which bind to collagenase IV. A buffered solution of collagenase IV, (10 mL, $10^{-3}\underline{M}$) (Salo *J. Biol. Chem.* 1983, 258, 2058) whose enzymatic activity appears to be important to tumor metastasis, is added to the hollow fibers of a third parallel binding chamber in the synthesis/trapping apparatus shown in FIG. 1, and the system allowed to incubate for a period of time necessary to produce specific binding peptides for collagenase IV. Procedures identical to those described for fibrinogen receptor concurrently identify peptides having high affinity for collagenase IV. The peptides having this property are screened for their ability to inhibit collagenase enzymatic activity using standard assays procedures for this enzyme. Those peptides expressing collagenase IV inhibitory activity, or synthetic modifications thereof, are potential candidates as injectables for reducing the likelihood of tumor metastasis.

The scrambling/trapping equipment assemblage lends itself to comparative identification of peptides having high affinity for closely related macromolecular systems. By way of example, hemoglobin and sickle hemoglobin, which differ by a single a.a., may be concurrently evaluated for the identification of high affinity peptides. A buffered solution of freshly prepared hemoglobin (10 mL $10^{-3}\underline{M}$), and sickle hemoglobin at an identical concentration, are separately loaded into the hollow fibers of two additional parallel binding chambers in the synthesis/trapping apparatus shown in FIG. 1, and the system allowed to incubate for a period of time necessary to produce high affinity peptides of interest. Comparison of the chromatography profiles of the high affinity peptides from the two hollow fibers containing the hemoglobin and sickle hemoglobin define, by difference, those peptides which bind to sickle hemoglobin but not to normal hemoglobin. Peptides having unique affinity for sickle hemoglobin, or their synthetic derivatives, are potential candidates for inhibiting the sickling process and, thus, for the treatment of sickle cell anemia. This result is also accomplished by using the series, ligand extraction/binding chambers 7 in FIG. 1 where hemoglobin is loaded into the extraction chamber 7, and the sickle hemoglobin into the assay chamber 8.

In another embodiment, we obtain selective net synthesis and identification of peptides which bind to phospholipase $A_2$.

A buffered solution of commercially available phospholipase ($10^{-4}M$) is added to the binding chamber in the synthesis/trapping apparatus shown in FIG. 1, and the system allowed to incubate long enough to produce a significant diversity of peptide products. Procedures identical to those described previously are used to identify high affinity ligands specific for binding to phospholipase $A_2$. Peptides with these properties are screened for their ability to modulate phospholipase $A_2$ activity using any of the standard assay techniques extant in the literature. Those peptides with such properties (or synthetic modifications thereof) are potential therapeutic agents on the basis of their anti-inflammatory characteristics.

Recovery and Characterization of High Affinity Peptides

The bound peptides may be removed from the target at any time. In one embodiment, the trap is itself removable from the trap compartment. After the trap is removed, it is placed in a buffer containing a suitable eluant, such as salt, to free the bound peptide from the target. Any eluant known in the chromatographic art may be used for this purpose, provided that it is capable of freeing the affinity peptide from the target. The freed binding peptide is then purified. Any method of purification known in the peptide purification and chromatography arts may be used for this purpose. In another embodiment, the fluid communication between the scrambling and trap compartments is entirely cut off, the trap compartment is flushed, and the affinity peptides still bound to the trap are freed with a suitable eluant. The affinity peptide is then removed with the eluant and purified as previously described.

The recovered peptide is then characterized as desired, e.g., by sequencing it on a peptide sequencer. Once the sequence of a peptide having a desired degree of affinity for the target is known, the peptide may be produced by any suitable technique, e.g., a Merrifield-type synthesis.

While the sequence of the binding peptide is its most important characteristic, other features, such as its molecular weight, amino acid composition, immunoreactivity, and the like, may be determined by art-recognized techniques, and such additional testing may have confirmatory value.

Monitoring the Scrambling and Trapping Reactions

It is likewise possible to estimate, by a variety of means, the degree of scrambling achieved. Some of the suitable methods are discussed below, however, the present invention is not limited to the enumerated methods.

The peptide size distribution within the scrambling compartment may be monitored by any means known in the art. In one embodiment, the compartment is equipped with a sampling means whereby a sample of the scrambling reaction product may be withdrawn. This sample is then analyzed by any method suitable for determining the peptide size distribution. A convenient method is gel permeation chromatography using polyacrylamide gels. Other methods include fast atom bombardment, electrospray mass spectrometry and peptide sequencing.

There is no practical method to assure that true global equilibrium has been reached in the scrambling reaction. This would require proof that all $10^{13}$ (in the case of 10 residues) possible peptides were present in equal amounts. The most practical definition of scrambling is simply the identification of peptides whose a.a. sequence is not found in the a.a. sequences of the starting proteins. The occurrence of a.a. scrambling in the peptides is also indicated by many other measures of free a.a. incorporation into, or peptide recombination of, existing peptides in the reaction mixture. The following qualitative and semi-quantitative analyses are useful in determining the extent to which the theoretical scrambling limit has been approached and thus an estimate of the numbers of peptides available for trapping. Initial assessment of a.a. scrambling in the peptides depends upon the fact that as scrambling occurs, chemical, as well as potential biological heterogeneity increases. Thus, the initial cleavage of a protein into fragments without scrambling produces a limited number of chemical entities, i.e. a few thousand for the small proteins such as casein and BSA. Chromatography (gel filtration, reversed phase, isoelectric focusing, ion exchange, normal phase, partition, etc.) of such a digestion mixture shows structure, i.e. peaks, by virtue of the relatively high concentration of a limited number of chemical entities.

As scrambling progresses, the chemical heterogeneity increases from a few thousand separate chemical entities to a maximum of about $10^{13}$ chemical entities for peptides 10 a.a. in length. As the chemical heterogeneity increases, there is a corresponding loss in chromatographic structure as the number of chemical entities increases and the quantity of any specific starting chemical entity decreases. In the limit, $10^{13}$ peptides, most differing slightly in their chromatographic behavior and each constituting only a very small equal fraction of the starting a.a. content, result in a chromatogram which is simply a broad hump lacking clearly defined peaks. Intermediate stages of scrambling are characterized by partial loss of chromatographic structure. Any increase in chemical heterogeneity. as measured chromatographically relative to that of the starting peptide mix, signifies qualitatively that a.a. scrambling is occurring.

The amount of a.a. scrambling in the peptides can be estimated by measuring the distribution of label with time in a scrambling reaction pulse labeled with dipeptide mixtures containing all a.a. These analyses depend upon the fact that at true global equilibrium, every a.a. free in solution and every a.a. at every position in every peptide in the mixture will have equal probability of access to the pulse labels. Though it is impractical to isolate every peptide and determine that the labels are evenly distributed over all possible peptides, as a first approximation, this can be done for the bulk properties of the heterogeneous mixture of peptides.

In this procedure, a mixture of dipeptides containing all twenty $^3$H-labeled a.a. (5 mCi, $10^{-7}\underline{M}$ total, adjusted to match the a.a. distribution of the peptide reaction mixture) are added to the reaction mixture ($10^{-2}$M amino acids) and the reaction allowed to incubate for a period of time. An aliquot of the reaction is removed and subjected to various forms of chromatography: gel filtration, reversed phase, isoelectric focusing, ion exchange, normal phase, partition, etc. The effluent from the chromatography matrix is analyzed for both 214 nM UV (all peptides) and $^3$H (those having undergone synthesis) detection. Any increase in chemical heterogeneity, as measured by $^3$H incorporation into new peptides derived from the unlabelled starting peptide mix, signifies qualitatively that a.a. scrambling is occurring. The greater the a.a. scrambling in the peptide mix, the closer the isotope and 214 M UV chromatographic profiles become. At true global equilibrium (100% scrambled state) the two profiles must be uniform over the entire UV spectral range.

Further definition of the amount of a.a. scrambling in the reaction mixtures can be obtained by determining the distribution of labeled a.a. at each position in the new peptide oligmers eluting from the various chromatographic procedures. At true global equilibrium, i.e. when complete a.a. scrambling in the peptides has occurred, the label will be evenly distributed over every possible a.a. compartment. (Compartments are defined as being the same relative position (i.e. 3rd residue from the carboxy terminus) in a heterogeneous mix of peptides.) The ratio of labeled a.a. to unlabeled a.a. will equal the starting ratio of added label to total a.a. content of the starting peptide mix of each of these compartments.

If this state has not been reached, the relative amounts of labeled a.a. at various positions in the peptide will differ from this theoretical amount. These differences can be used to further estimate the degree to which the system has approached the true global equilibrium state. The total molar concentration of a.a. in the starting mixture is the sum of starting peptides and those added to maintain a given average peptide length The analysis is carried out by sequentially degrading the peptides in the various chromatographic fractions enzymatically, using peptidase hydrolysis, or chemically, using Edman degradation, and subsequently measuring the amount of label released as each a.a. residue is released from the peptides. The amount of scrambling, i.e. the extent to which true global equilibrium has been reached, is defined as the percentage of this observed ratio over that theoretically possible (i.e. $10^{-5}$). Values from zero to $10^{-5}$ are possible, reflecting the degree to which scrambling has occurred.

It is desirable to be able to determine routinely whether the components and conditions of a scrambling reaction, i.e., particular enzymes, enzyme concentrations, peptide feed stock, amino acid composition of peptide feed stock, ionic strength, pH, temperature, etc., are appropriate to generate high affinity peptides which in turn will bind to a specific receptor or macromolecule. One means of determining that the scrambling reaction has succeeded in producing such peptides is to remove the receptor from the reaction at an arbitrary time, liberate the bound peptides and perform a laborious analysis. This destroys the receptor, with no guarantee that high affinity peptides have in fact been synthesized and trapped by the macromolecule. Furthermore, there is no guarantee that any high affinity peptides have been generated, and that they bind to functional sites on the macromolecule.

For these reasons, several methods have been developed to permit intermittent (or continuous, if a flow-through detector is employed) monitoring of the binding compartment to establish that amino acid scrambling/ macromolecular trapping of biologically active peptides is proceeding. One of these methods may be applied as an initial screening procedure on a very small scale, thereby minimizing the quantities of receptor required to establish optimum reaction conditions.

The monitoring methods require a ligand of known affinity for a functional site on a soluble target molecule (a.k.a. "receptor", though not limited to conventional receptor proteins, and typically but not necessarily a macromolecule). In one embodiment, both the ligand and the receptor are free in solution. In this case, the receptors would be preincubated with a labeled ligand. If a peptide displaced the ligand from the receptor, free labeled ligand would appear in solution. The reaction compartment would be a three-component mixture of free ligand, ligand-receptor complex and peptide-receptor complex. Aliquots of the solution in the reaction component could be withdrawn, and chromatographically separated into the aforementioned components. The amount of label in either the free ligand fractions or in the ligand-receptor complex fractions could be measured directly. The peptide-receptor complex could be labeled, e.g., with a labeled antibody, and then assayed in the peptide-receptor complex fractions.

If the ligand was fluorescently labeled, it might be possible to spectroscopically distinguish free and bound ligand through its effects on the fluorescence, and thereby avoid chromatographic separation, or even withdrawal of sample.

In a second embodiment, either the ligand or the receptor is immobilized on a support. The support may be, e.g., agarose beads, or any other support customarily used in binding assay or affinity chromatography procedures. The linkage may be covalent or noncovalent, see, e.g., Colawick, et al., "Immobilized Enzymes", in Meth. Enzymol., Vol. 44 (1976). The formation of bound peptide is then monitored by detecting the release of receptor, if the ligand is immobilized, or of the ligand, if the receptor is immobilized. This second embodiment does not require a chromatographic separation.

For example, the ligand is first immobilized on a solid matrix (e.g, agarose beads) using standard procedures. This ligand-bead complex is incubated with the target (e.g., macromolecule) in the binding compartment such that most of the target is bound to the ligand. The degree of binding will be determined by the immobilized ligand concentration, the affinity of the ligand for the target binding site, and the target concentration in the binding compartment. The actual concentration of free target can be experimentally established by standard assay methods. The binding compartment is then placed in communication with the scrambling compartment, and the scrambling reaction is allowed to proceed. Periodically, samples (which are aliquots representing an insignificant fraction of the total volume) of the soluble fraction of the binding compartment are withdrawn and assayed for the presence of free receptor.

If the target has an assayable activity, it may be measured directly. For example, target enzyme in the sample aliquot may be measured by providing a suitable substrate and assaying for the appearance of the enzymatic product. If it may be done without impairing the binding characteristics of the target, the target may be radiolabeled before it is placed in the binding compartment, and the level of radioactivity in the sample aliquot measured. If labeling the target before it is placed in the binding compartment would alter its binding characteristics, it may be labeled after it is withdrawn in the sample aliquot, e.g., with a labeled antibody. In any event, any method of measuring the amount of target in the aliquot taken from the soluble fraction of the contents of the binding compartment, which does not substantially interfere with the purpose of the invention is suitable for use as part of this monitoring method.

Under these conditions, the concentration of free target in the binding compartment will increase only if the following conditions are met: 1. the scrambling reaction generates a peptide which binds to the site occupied by the immobilized ligand, and/or the scrambling reaction generates a peptide which binds to an allosteric site on the receptor, thereby decreasing receptor (target) affinity for the immobilized ligand; and 2. the peptide which directly competes for the immobilized ligand binding site has a $K_d$, which approximates or exceeds the $K_d$ of the immobilized ligand. Alternatively, a peptide of lesser affinity for the immobilized ligand binding site will also lead to increased free receptor if it is produced in sufficiently high concentrations to compensate for its lesser affinity.

If the assay does not indicate an increase in free receptor concentration as a function of time, it can be concluded that the scrambling reaction is not generating peptides of biological interest for that receptor and that the reaction conditions must be altered. Such alterations might include the addition of more or different enzymes, the addition of different peptide feed stock, changing the pH of the reaction solution, etc. Once specific scrambling reaction conditions are altered, the binding compartment is again sampled for free receptor at appropriate time intervals. This monitoring and editing process is repeated as required to establish scrambling reaction conditions which yield peptides capable of binding to the functional or allosteric binding sites. Since the amount of receptor required for each screening process is minimal, multiple scrambling/binding reactions can be simultaneously monitored, thereby decreasing the time required to determine optimum scrambling/trapping conditions.

Once such conditions are established, the reaction is scaled-up to the level which will generate sufficient amounts of receptor-bound peptide(s) to permit separation and analysis by conventional procedures. This can be performed in the absence of immobilized ligand, and in most cases would only require increasing the receptor concentration in the binding compartment.

It should be noted that the use of immobilized ligands for the monitoring process is feasible only when ligands against a functional receptor site have been previously identified. For most receptors, this will be the case. However, when such ligands are unavailable or cannot be employed for practical reasons, other approaches may be taken, e.g., monoclonal antibodies or anti-peptide antibodies directed against the functional site of the receptor protein. If antibodies are utilized, it must be recognized that scrambled peptides may not only bind to the functional binding site on the receptor, but may also bind to the functional site on the antibody. The production of such anti-antibody peptides could therefore lead to the appearance of free receptor in the binding compartment, even though functional antireceptor peptides were not produced in the scrambling reaction. If this phenomenon occurred to an appreciable extent, the scrambling reaction would inadvertently be optimized to favor the synthesis of anti-antibody peptides. On the other hand, identification of these peptides would provide valuable information concerning the linear peptide sequence that mimics the receptor functional site. Based on this information, predictions could be made concerning the sequence of complementary anti-receptor peptides, which in turn could be optimized through their use as immobilized ligands as described above.

Recognizing the above limitations, using this process to monitor the scrambling reaction provides the following advantages: 1. "On line" information can be obtained to direct modification of the scrambling reaction conditions; 2. Much smaller quantities of receptor are required to establish the scrambling conditions in which high affinity peptides against a particular receptor are generated; 3. The time required for the scrambling reaction to generate detectable amounts of high affinity peptides is substantially less than that for the previously described technology. This decrease in time is directly proportional to the reduced concentration of receptor, which can be used in the monitored reaction, i.e., if $\frac{1}{100}$ of the receptor concentration is utilized, high affinity peptide production can be detected in $\frac{1}{100}$ the time; 4. The specific affinity of the immobilized ligand determines the affinity threshold of peptides which will cause displacement of the receptor; 5. The scrambling reaction can be optimized for peptides which bind to or modify the biologically functional site of the receptor; and 6. The monitor reaction will yield the rates of synthesis/trapping of high affinity, biologically relevant peptides. This information can, in turn, be used to predict the minimum time required for the scaled-up reaction to generate identifiable amounts of receptor-bound peptide.

It should be appreciated that the procedures set forth above as a monitoring method may also be used to screen for a peptide which would interfere with a ligand/receptor interaction.

The following examples are offered by way of illustration, and are not in any way limiting. Those skilled in the art will recognize that different proteolytic enzymes or combinations of proteolytic enzymes may be employed, that reaction times and concentrations of reagents may to some extent be varied, that useful peptides of different sizes may be generated, and that other means of separating the "scrambling" and "selective" systems may be employed.

Abbreviations

The following abbreviations are used hereafter: a.a= amino acids, W=tryptophan, E=glutamate, F=phenylalanine, Y=tyrosine, L=leucine, S=serine, G=glycine, I=isoleucine, K=lysine, V=valine, A=alanine, $\underline{M}$=molar, g=grams, mg=milligrams, kDa=kilodalton, 2-D SDS-PAGE=two-dimensional sodium dodecyl sulfate polyacrylamide gel electrophoresis.

EXAMPLE 1

Experimental Demonstration of "Scrambling" of Proteins and Peptides by Proteases To date, the enzymically-catalyzed scrambling of peptide primary structure has been conclusively demonstrated in a number of experimental systems. Evidence for the occurrence of scrambling is available at three levels of surety, as outlined below.

The first and most definitive proof of enzymic scrambling lies in the unambiguous determination of primary structures of peptides isolated from reaction systems, and the demonstration that said sequences are new and unique relative to the known structures of the substrates and enzymes. This level of proof has been obtained in simple model reactions with dipeptide and tripeptides substrates using the enzymes bromelain, pepsin, and thermolysin (See Exs. 1D and 1F).

The second level of proof is derived from the redistribution of a radioisotope label originally confined to a single homogeneous dipeptide substrate across a broad array of reaction products. This has been observed for simple systems using the $^3$H-labeled dipeptides Trp-Glu and Trp-Tyr, and the enzymes papain, pepsin (Example 1B), and thermolysin and bromelain together. Additionally, it was shown that pepsin could incorporate $^3$H from isotopically labeled Trp-Glu into peptides generated by simultaneous hydrolysis of casein (Example 1A). It is difficult to conceive of a mechanism other than scrambling of amino acid sequences that could account for the dispersal of radiolabel from a single starting material into multiple products across the chromatogram.

The third line of evidence comes from the generation of multiple new peaks observed in the reaction profiles of simple experimental systems utilizing dipeptide substrates and single proteases. The absence of co-chromatography peaks from appropriate substrate and enzyme controls implies that the novel metabolites arose through successive rounds of ligation and hydrolysis of the initial substrate. In a number of cases, new products were tentatively identified by means of co-chromatography with authentic standards (see FIG. 5). In addition to the four enzymes discussed in the preceding sections, this level of proof has been obtained with trypsin, chymotrypsin, subtilisin BPN' ("Nagarose protease"), dipeptidyl peptidase IV, ("cathepsin C"), and proteinase K.

In summary, we have corroborative evidence of this type for nearly 300 simple model reactions utilizing 9 different proteases over a broad spectrum of experimental conditions. In these experiments, we can show that 19 of the 20 amino acids have been moved by scrambling. We have no conclusive proof for the specific movement of proline, having moved it only as a residue in a larger block, but we have no reason to doubt that it can be moved by scrambling.

A. (Casein: WE)/Pepsin

Casein (0.5 mM) and pepsin (0.25 mM) were incubated together with tritium-labelled WE dipeptide in 50 mM potassium phosphate buffer (pH 5.0) at 22° C. Samples were then subjected to reverse phase HPLC to separate the peptides and analyze them for tritium content. After 1, 5 and 7 days of reaction time, tritium was incorporated into multiple new peptides, indicating that pepsin can both digest the casein to yield peptides and then add amino acids from the dipeptides to these peptides.

B. (WE)/Pepsin or Papain

Tritium-labelled WE dipeptide (50 mM, 0.9 $\mu$Ci) was incubated with either pepsin (0.25 mM) or papain (0.25 mM) in 50 mM potassium phosphate (pH 5.0) at 22° C. When papain was used, it was first activated at 22° C. for 2 hours in 50 mM KCN, 15 mM EDTA, 60 mM acetate in water. Peptides were separated and analyzed as in Example 1A. Formation of multiple new peptides was observed after 1 or 5 days of reaction, demonstrating that both papain and pepsin are capable of synthesizing new peptides.

C. (EW, WE, FY)/Pepsin, Papain

Dipeptides EW, WE and FY were incubated with pepsin and papain under the conditions described in Example 1B. After 1 day multiple new peptide products were produced in numbers exceeding the sum of peptides produced from individual dipeptides.

D. (YYF, VAAF)/Pepsin

The tripeptide YYF (50 mM) was incubated with pepsin under conditions described in Example 1A. Alternatively, tripeptide YYF (25 mM) and tetrapeptide VAAF (25 mM) were coincubated with pepsin (0.25 mM). Samples were analyzed for peptide products at hourly intervals between 1 and 24 hours, and at 36 hours. Single amino acids, dipeptides, tripeptides, tetrapeptides and pentapeptides were present in all samples, with species having varied amino acid sequences being present. Both inter- and intrapeptide amino acid exchange was observed. The product profile changed dramatically between 1 and 24 hours. The peptide profiles at 1 and 36 hours for the YYF/pepsin scrambling system is shown in FIG. 14. This demonstrates that pepsin catalyzes scrambling of peptides, i.e., rearranging of amino acids within and among peptides in a dynamic equilibrium between hydrolysis and formation of peptide bonds.

E. (LY, LSF), (WE, LSF), (WE, GGI), (WE, GLY)/thermolysin; (LW, KYK), (WF)/bromelain Di- or tripeptides (50 and 25 mM respectively) LY and LSF, WE and LSF, WE and GGI, or WE and GLY were incubated with thermolysin (0.1 mM) at 22° C. in 50 mM potassium phosphate (pH 8.0). Alternatively, dipeptides LW (50 mM) or WF (50 mM) were incubated with tripeptide KYK (25 mM) and bromelain (0.1 mM) in 50 mM potassium phosphate (pH 8.0), 5 mM 2-mercaptoethanol. After 24 hours multiple new peptides are formed that are absent when only the dipeptide or tripeptide alone is incubated with thermolysin. This demonstrates that more complex mixtures of reactant peptides produce disproportionately more complex peptide products.

F. (WE, LSF)/thermolysin

Dipeptide WE (50 mM) and tripeptide LSF (25 mM) were co-incubated with thermolysin (0.1 mM) under conditions described in example 12. After five days a multiplicity of new larger peptides of various sequence were obtained. One such peptide contained isoleucine, presumably from the thermolysin. Thus the smaller peptides, as well as the protein are capable of donating a.a. that can be incorporated into larger scrambled peptides.

EXAMPLE 2

MASS DIVERSITY: EXPERIMENTAL AND PREDICTED BY COMPUTER MODEL

The mass diversity in a scrambling reaction with bovine serum albumin (BSA) as the substrate was compared with that predicted by a computer model (see below). In the latter, the initial substrate was an eight-residue poly-amino-acid. Both the model and BSA experiment indicate that 1) the scrambling reaction does not wind down to single amino acids within 5 days 2) there is an increase in peptide diversity. The following two sections describe the experimental results and the computer model.

Mass Diversity Experiment

Protocol

BSA at a concentration of 1 mM was digested with bromelain, subtilisin BPN', and thermolysin, each at a concentration of 0.2 mM, in 50 mM disodium phosphate at pH 7.20, supplemented with 100 mM sodium chloride and 5 mM dithiothreitol. Samples of the digest were taken every 24 hours for five days and subjected to reversed phase HPLC ($C_{18}$). This complex reaction was sampled by monitoring three windows representative of the total reversed phase profile. The windows (from 11–12 min, 22–23 min, and 33–34 min being windows 1, 2 and 3, respectively) were chosen with the object of sampling the diversity of size and relative hydrophobicity present in the total profile. A total of 600 μL of reaction was taken each day and fractionated on the $C_{18}$ column (in three separate injections of 200 μL each), with the three 1-minute windows collected manually each run. Samples were frozen at −80° C. and lyophilized to dryness in an evacuated centrifuge. The samples were then reconstituted in 100 μL of deionized water and analyzed by capillary electrophoresis (CE) and fast atom bombardment mass spectrometry (FAB MS).

Results

Capillary electrophoresis analysis reveals that molecular species are in a constant state of flux with time (FIG. 6). Particular peaks can be followed from Day 1 through to Day 5, and can be shown to increase or decrease with respect to time while other species disappear or appear as the reaction proceeds. There is no evidence suggestive of a collapse to a smaller number of molecular species. The FAB MS data strengthen this impression, showing that for a slight decrease in the overall mass intensity, there is, if anything, a net increase in the molecular diversity of the profile in the 300–1500 dalton range. A blow-up of the 900–1100 dalton range for window 2 at Days 1 and 5 illustrates this pattern. FIG. 7 shows the mass diversity in this range, as measured by FAB MS, on day 5.

Conclusions

1) There is no strong evidence for time-dependent progress toward increased amounts of lower mass species at the expense of higher mass species. This is supported by the absence of large increases in the mass intensities of the lower mass species at extended times. This, in turn, is incompatible with a reaction model in which the proteases are active strictly in degradative mode; thus, with both hydrolysis and synthesis occurring simultaneously, scrambling must be occurring.

2) While overall mass intensity in the 900–1100 dalton range remains essentially unchanged, there are clear indications of movement between species and even an increase in the number of species visible in the windows. The increase of species diversity with time is corroborative evidence for the occurrence of synthesis, and hence, scrambling, in the reaction.

3) Both the CE and FAB MS data clearly indicate a grand scale of molecular diversity. This suggests that such diversity could not arise simply through cleavage of the four proteins into smaller and smaller pieces.

Computer Model to Evaluate the Number and Length of Peptides in a Scrambling Reaction Simplifications and Assumptions As mentioned above, modeling of the scrambling reaction was simplified by the use of an eight residue poly-amino-acid. With this simplification, the hydrolysis rate is equal for each of the L-1 amide bonds of a peptide of L residues. The reaction can be further simplified by making the following assumptions.

1) The synthesis rate is independent of peptide length, L.

2) Single amino acids do not take part in synthesis. (All evidence so far indicates that this is a valid assumption.)

3) There is no hydrolysis of dipeptides. This is a reasonable approximation when considering the nature of substrate recognition and binding in the active site (most proteases recognize 4–7 additional residues around those involved in the scissile peptide bond). There are greater than four dipeptide-active site configurations in which a dipeptide is not placed directly over the catalytic site; only one configuration, over this bond, leads to hydrolysis. In contrast, since it is possible to bind on either side of this site, there are two configurations in which dipeptides may take part in synthesis. With these points in mind, it may be assumed that dipeptides take part in synthesis but not in hydrolysis.

4) By assuming a 6-residue binding site of enzyme, hydrolysis is proportional to L-2 for 2<L<7 and constant for L>5. For example, the hydrolysis rate is 4 times higher for a peptide of L=6 [6−2=4] than for a peptide of L=3 [3−2=1]. This assumption takes into consideration the higher probability of longer substrates binding over the catalytic site.

5) Finally, the model is simplified by assuming the maximum peptide length is 16 amino acid residues.

Scrambling Reactions

A flow-diagram of the computer program is shown in (FIG. 8). In this model, only the scrambling reaction is studied. This comprises synthesis and hydrolysis, not binding to a macromolecule. The reactions considered in the model are listed below.

Peptides may accumulate and be depleted through both synthetic and hydrolytic reactions. In synthesis, accumulation of peptide $L_c$ occurs by reaction of two peptides of length $L_b$ and $L_c$, where $L_a = L_b + L_c$; depletion of peptide $L_a$ occurs by condensation with peptide $L_d$ to form peptide of length $L_a + L_d$, not to exceed 16 amino acid residues (L<17). Similarly, in hydrolytic reactions peptide $L_a$ accumulates through hydrolysis of peptide of length>$L_a$ and in turn is depleted through cleavage of itself.

Results

From the results plotted in FIG. 9, several features of the scrambling reaction are apparent. The reaction does not rapidly wind down to free amino acids. After 5 days, free amino acids are only 25 mole %. This allows for a broad time range from 2–5 days where the concentration of scrambled products does not change appreciably. As shown in the above plot, there exists a maximum scrambled-product concentration at 40–100 hr. The model prediction is consistent with the preliminary experimental results with BSA (see above and Table 1).

The lower plot in FIG. 9 indicates the amount of scrambling products available for analysis in a typical substrate system, in this case 10 mM octapeptide of eight different amino acid residues. From the simulated reaction shown in the upper plot, the lower plot was determined as follows. For peptides of 7, 8 and 9 residues the total concentration was evaluated by multiplying the mole % in the upper plot by the total mass present (i.e. 10 mM octamer, average molecular weight of each residue 114 daltons). To determine the concentration of a sequentially unique peptide, the concentration of a peptide of length L is divided by the total possible combinations. In this case there are $8^7$, $8^8$ and $8^9$ possible peptides of lengths 7, 8 and 9 when starting a substrate of 8 different amino acids. Table 2 summarizes these results.

The lower concentration of the nonamers compared with heptamers is due to lower production in the reaction and, more significantly, the greater number of possible nonamers. As mentioned earlier, in the model reaction there are $8^7$ and $8^9$ possible combinations of heptamers and nonamers, so that there are 64 (=$8^2$) times as many unique heptamers. In other words, the concentration of sequentially unique nonamer is 64 times less than for a heptamer for equal molar production of total peptide. Table 2 does not indicate decrease in peptide diversity for larger peptides, but only that there is a lower concentration of these for analysis.

The lower limit of detection for CE is ca 0.2 pmole. At 3 ng/L a nonamer with an average MW 1040 daltons, would be detectable by lyophilizing 600 mL down to dryness and resolubilizing in 500 nL, yielding enough for the 60 nL injection volume.

Conclusions

1) As in the Mass Diversity Experiment section above, the above model indicates that there is no rapid degradation of substrates to free amino acids, which do not take part in the scrambling reaction.

2) Existing between 40–100 hr, the maximum production of peptides of 3–7 residues is 40 mole %, of 9–16 residues, 12 mole %. 3) With manageable reactor volumes, e.g., 600 mL, all possible nonapeptides are detectible by CE.

Amount of Scrambled Products as a Function of Synthesis to Hydrolysis Rate

It may be argued that in proteolytic reactions there will always be some synthesis of peptides even in those reactions which are nominally hydrolytic. This would meet one of the criteria for scrambling of peptides, that is synthesis and hydrolysis rates occurring simultaneously; however, it would fail to produce a sufficient amount of scrambled products since the synthesis rate is drastically lower than the hydrolysis rate. To allow for analysis of bound products the trapped ligands (i.e., those that have be scrambled) must be present in sufficient amounts, not minute amounts as would occur in a hydrolytic reaction with inadvertent synthesis.

The proposed technology gears the reaction towards synthesis so that a significant amount of synthetic material is produced. As can be seen by the computer model below, the concentration of scrambled products is greatly decreased under low synthesis conditions. The extent of synthetic products is shown in Table 3 for optimized synthesis (large ratio of synthesis rate to hydrolysis rate) and inadvertent synthesis during nominal hydrolysis (low ratio of synthesis rate to hydrolysis rate).

The following model along with the assumptions is similar to that described in the Molecular Diversity section. The conditions are slightly different:

Maximum peptide length 8 residues

Tripeptide substrate

The extent of synthesis in the model is measured by summing up the maximum mole fractions of peptides of length 4 through 8 which are those peptides which can only be formed by synthesis. These results are listed in Table 3 and plotted in FIG. 13.

Table 3 shows that the amount of large peptides, those of interest, decreases drastically with decreased synthesis rate. For example, the maximum mole % of peptides with 4–8 residues is over 1000 times less at synthesis rate/hydrolysis rate equal to 100% compared to 0.05%; it is nearly 400 times greater for a ratio of 25% compared to 0.05%.

It is clear that inadvertent synthesis, with the ratio of synthesis rate to hydrolysis rate less than 0.05%, is not as productive as an optimized scrambling reaction with a higher ratio, e.g., greater than 25%. In the former, scrambled products can be over two orders of magnitude less than in the latter. Concomitant with the larger amount of scrambled products is a larger amount of ligand. For practicable analysis of bound products, it is necessary to have as much ligand present as possible. As seen above, an optimized synthetic system produces much more than a nominally hydrolytic system with inadvertent synthesis. Therefore, the latter will not be as effective in producing ligands as the proposed technology which does optimize scrambling.

Scrambling Calculations for Peptide Amplification

For a 1 liter reaction containing 1 mole of scrambled peptides (up to 10 amino acids in length) there would theoretically be $10^{13}$ individual peptides each with a concentration of $10^{-13}$ molar. In a static situation in which the absolute amount of each peptide remains constant, the maximum amount of a single peptide which could be trapped by a macromolecule (at a concentration $>10^{-13}$ molar) is therefore $10^{-13}$ moles. However, if the concentration of each peptide is maintained at $10^{-13}$ molar (by random peptide synthesis), the maximum amount of a single peptide which can be trapped is both a function of the Kd of the peptide for the macromolecule and the amount of macromolecule.

```
Kd = dissociation constant
[M] = concentration of macromolecule
[P] = concentration of peptide in reaction
[MP] = concentration of macromolecule-peptide complex
              Kd = [M][P]/[MP]
assume:   [M] = 10⁻⁶ M
          [P] = 10⁻¹³ M
          [Kd] = 10⁻⁹
then:     [MP] = 10⁻¹⁰ M; an amplification of 1000x
          relative to 10⁻¹³ M
assume:   [M] = 10⁻⁶ M
          [P] = 10⁻¹³ M
          [Kd] = 10⁻⁸
then:     [MP] = 10⁻¹¹ M; an amplification of 100x
assume:   [M] = 10⁻⁶ M
          [P] = 10⁻¹³ M
          [Kd] = 10⁻⁷
then:     [MP] = 10⁻¹²¹ M; an amplification of 10x
```

Therefore, the higher the affinity of the peptide for the receptor, the greater the amplification factor. Since peptide analysis and sequencing (with present technology) is limited to roughly $5 \times 10^{-11}$ moles of a given peptide, selective amplification of peptide accumulation is a prerequisite to the feasibility of selecting and detecting measurable amounts of a particular peptide.

EXAMPLE 2A

Demonstration of Trapping of Specific Binding Peptides by a Macromolecular Target FY (50 mM) was incubated with pepsin (0.25 mM) for five days. The scrambled mixture was ultrafiltered to remove components greater than 1000 Daltons molecular weight, including the pepsin. The passthrough (low MW) fraction was then incubated with BSA (50 mM), casein (50 μm) or fibrinogen (50 μM) for 45 minutes and the mixture was then ultrafiltered again. The high MW fraction was collected. the filter was washed to remove loosely adhering peptides, the material remaining on the filter was resuspended, and the more strongly binding peptides remaining were then released by heat denaturation of the protein. A third ultrafiltration then separated the binding peptides from denatured protein. FIG. 15 shows the reverse phase HPLC elution profiles of the peptides found to bind each of the proteins BSA, casein and fibrinogen. It should be noted that even though the screened mixture was the same in each case, different peptides were bound, depending on the choice of target macromolecule.

EXAMPLE 3

Demonstration of Equilibrium Shifting by a Macromolecular Sink

A. Casein (0.5 mM) was incubated with pepsin (0.25 mM) in 50 mM potassium phosphate (pH 6.3), 5 mM EGTA, 2 mM $MgCl_2$ at 22° C. in the presence of a dialysis bag having a 1000 dalton cut-off and containing iso-osmolar buffer with or without fibrinogen (0.03 mM). After 1 to 93 hours low molecular weight products are detectable in the dialysis bag in either case. The products in the dialysis bag were different in the presence of fibrinogen than its absence, and the quantity of at least one product increased as a function of time in the presence of fibrinogen. This demonstrates that (1) low molecular weight products resulting from proteolytic digestion of casein can diffuse across a semi-permeable barrier, and (2) the presence of a macromolecular sink across the semi-permeable barrier from the scrambling reaction can shift the equilibrium of the scrambling reaction to favor synthesis of specific products.

B. Dipeptide FY (50 mM) was incubated with pepsin (0.25 mM) in 50 mM potassium phosphate (pH 5.0) at 22° C. for 24 hours. The reaction mixture was then placed outside a dialysis bag with a molecular weight cutoff of 1000 daltons. The dialysis bag contained 1 mL of 50 mM bovine serum albumin (BSA) in iso-osmolar buffer. After 5 days, aliquots from inside the dialysis bag were filtered through a 10,000 dalton cutoff filter membrane, which was then washed with iso-osmolar buffer. The membrane retentate was resuspended in iso-osmolar buffer and denatured at 100° C. for 15 minutes to separate the specific binding peptide from the bound complex then filtered through a 1000 dalton cutoff filter. Filtrate was subjected to reverse phase HPLC for peptide separation and analysis, using peptide standards. When fibrinogen or casein was substituted for BSA as the macromolecular sink, different specific binding peptides were obtained. This demonstrates that a receptor macromolecule can exert an influence on the bound product profile observed for the reaction via the specificity of peptide binding to the given receptor.

EXAMPLE 4

Scrambling peptides and screening for binding to fibrinogen receptor ($GpII_hIII_a$)

Introduction

The heterodimer glycoprotein $GpII_hIII_a$ is the major cell surface integrin of platelets. $GpII_hIII_a$ is the receptor for fibrinogen and other adhesive proteins, and it plays a central role in platelet aggregation and adhesion to the subendothelium. $GpII_hIII_a$ is known to bind many Arg-Gly-Asp (RGD) containing peptides such as RGDW [SEQ ID NO:1], RGDY [SEQ ID NO:4] and RGDM [SEQ ID NO:5] which bind with affinities in the range of $10^{-4}$–$10^{-6}$M. Therefore, in an experimental system consisting of an enzymic reaction capable of producing RGD peptides by scrambling, dynamically coupled to a $GpII_hIII_a$ binding system, isolation of any RGD peptides bound to the receptor would constitute direct proof of the technology.

Experimental Procedures

The receptor was purified to homogeneity by the criterion of gel electrophoresis. The receptor was concentrated by centripetal ultrafiltration using Centricell (MWCO 30000); concentrated receptor has an absorbance of 0.587 at 595 nm in Bio-Rad assay, corresponding to an apparent concentration of 600 µg/mL using a standard curve derived from BSA. The receptor preparation was dialyzed against binding buffer prior to use in the peptide binding experiment.

A mixture of peptides (RD, WY and GSF, 25 mM each) and enzymes (thermolysin and bromelain, 0.1 mM each) were incubated in 50 mM sodium phosphate buffer at pH 7.4, supplemented with 150 mM sodium chloride, 2 mM magnesium chloride and 5 mM octyl glucoside.

The binding chamber, separated from reaction chamber by a semipermeable membrane (MWCO 1000), contained 2 mL of concentrated receptor (or BSA, 0.7 mM) in the same buffer. After 40 hr incubation, the mixture in the binding chamber was collected and subjected to 4 washes using a microconcentrator (MWCO 30000). Receptor was resuspended, heat-denatured and filtered (MWCO 10000) again to remove denatured protein. Filtrates containing the released peptides were then analyzed by reversed phase HPLC (see Table 4) and a fraction at t=21'18"–22'05" (RGDW region of chromatogram, as identified by an authentic standard, was collected, dried and analyzed on capillary electrophoresis (CE).

Capillary electrophoresis analyses were done on a Beckman P/ACE 2100 instrument using a fused silica capillary, 75 µm×57 cm with 0.1M sodium phosphate buffer, Ph 2.5 as the electrolyte. The analytical runs involved 10 sec pressure injections (60 nL) of the sample, followed by a 1 sec pressure injection of a 90 µg/mL aqueous solution of Arg-Gly (internal standard). The separation was generally 40 min at 15 kV. Attempts were made to identify Arg-Gly-Asp-Trp (RGDW) [SEQ ID NO:1] in the sample mixture by coinjection of the appropriate standard. This involved a 10 sec pressure injection (60 nL) of the sample followed by a 1 sec pressure injection of a 1.9 µM aqueous solution of tetrapeptide RGDW.

Results and Discussion

The HPLC fraction collected from the RGDW [SEQ ID NO:1] region, when analyzed by CE (FIG. 10), showed an unknown peak with a retention time (14.82) corresponding to the retention time of RGDW standard. Furthermore, when this fraction was co-injected with authentic RGDW, the unknown peak co-eluted with the RGDW (FIG. 11). The presence of RGDW as a bound product is strong evidence of peptide scrambling in the enzymic reaction and the trapping of the peptide ligand in the system by the receptor.

Moreover, when BSA was used as a binding macromolecule in the same binding system there were no peptide products isolated that corresponded to RGDW. This indicates specificity of the binding of ligands to their respective proteins.

EXAMPLE 5

Scrambling of a GPR-Spiked Starting Mixture and Screening for Binding to Fibrinogen Introduction Human fibrinogen, a soluble protein present in normal blood plasma, plays an integral role in both hemostasis and thrombosis. Fibrinogen is converted to the insoluble fibrin matrix of blood clots by thrombin and Factor XIII. Initially, fibrinopeptide A is cleaved from the amino-terminus of the Aα chain of fibrinogen to form fibrin monomers. Upon release of fibrinopeptides, fibrin monomers spontaneously polymerize to form a non-covalently bonded gel. Fibrin polymerization results from the interaction of the newly exposed amino-terminus of the Aα chain (beginning with the sequence Gly-Pro-Arg (GPR)), and the carboxy-terminal portion of the gamma chain of fibrin(ogen).

It has been demonstrated that synthetic peptides beginning with the sequence GPR will bind to fibrinogen and prevent fibrin polymerization. The peptides GPR, GPRP [SEQ ID NO:6], and GPRV [SEQ ID NO:7] bind to human fibrinogen with affinities of 50, 25, and 100 µM, respectively, and inhibit fibrin polymerization (A. P.

Laudano and R. F. Doolittle, Biochemistry, 19 (1980), 1013–1019). The current lead optimization experiment was unique GP to determine whether unique GPR-like peptides could be created from a reaction "seeded" with GPR and if these new products could then bind to fibrinogen.

Methods

Prior to use in the dynamic binding reaction, human fibrinogen was dialyzed and treated with a serine protease inhibitor (phenylmethylsulfonyl fluoride) in order to eliminate low molecular weight peptides and contaminating plasmin activity. The pre-treated fibrinogen (10 mg/mL) was added to a dialysis bag (MWCO 3500). This dialysis bag was immersed in a solution containing thermolysin, bromelain (each at 0.1 mM), GPR (4 mM), 0.004% sodium azide, and 1.6% trypsin-BSA hydrolysates (molecular weight less than 1000). Control conditions consisted of: 1) fibrinogen incubated with all reactants except GPR and, 2) fibrinogen incubated with buffer. The buffer for all solutions was a 50 mM sodium phosphate solution with 0.3M NaCl, pH 7.0.

After 16–18 hours, the contents of the dialysis bag were fractionated on a PD10 gel filtration column (Pharmacia) and the high molecular weight fraction collected in order to separate bound from free products. A portion of this material was denatured by boiling and then ultrafiltered (MWCO<3000). This initial ultrafiltrate represented bound material which was not dissociated from fibrinogen after one PD10 wash. The remaining non-denatured fibrinogen was subjected to further gel filtration washes followed by denaturation and ultrafiltration.

Ultrafiltrates were concentrated and subjected to reversed phase HPLC (Waters DeltaPak C18V column). Peptides were eluted in a gradient of 0–60% acetonitrile in 0.1% TFA. The elution times are given in Table 5. HPLC fractions were collected, concentrated, and analyzed by capillary electrophoresis (CE).

Capillary electrophoresis analyses were done on a Beckman P/ACE 2100 instrument using a fused silica capillary 75 μm×57 cm. The electrolyte was 0.1M sodium phosphate buffer, pH 2.5. The analytical runs involved 10 sec pressure injections (60 nL) of the sample, followed by a 1 sec pressure injection of a 90 μg/mL aqueous solution of Arg-Gly (internal standard). The separation was generally run for 40 min at 15 kV. For fraction collection, a vial with 10 μL of 25 mM sodium phosphate, pH 2.5 was positioned at the capillary outlet at the appropriate time. Multiple peak collections were made into the same vial. After fraction collection was complete, a reinjection of the collected material was made to verify homogeneity.

Analysis of the biological activity of GPR-like peptides was performed with a spectrophotometric assay of fibrin polymerization. In this procedure, all solutions were prepared in a buffer consisting of 10 mM HEPES, 0.1M NaCl pH 7.4. Fibrinogen (0.5 mg/mL) was pre-incubated with calcium chloride (1 mM) at 37° C. Vehicle or peptide was added followed by thrombin (0.5 U/ml). Fibrin polymerization was monitored on the basis of increasing turbidity. Data are expressed as the optical density (350 nm) at t=2 minutes following thrombin addition.

Results

Two minute HPLC fractions representing material bound to fibrinogen were screened on CE to determine which peaks were not present in either control condition. Three of these GPR dependent peaks were collected via preparative capillary electrophoresis and sent to outside facilities for amino acid sequencing. Amino acid sequencing of the collected material revealed the tetrapeptides GPRL [SEQ ID NO:8] and GPRF [SEQ ID NO:9] and the tripeptide LPK. In addition, a GPR-independent peak was also collected and found to have the sequence DKPDNF [SEQ ID NO:3] (FIG. 12).

Analysis of washed fractions by CE showed that GPRL had a relatively low affinity in that the associated peak height, diminished quickly with additional gel filtration. In this regard, the peak height associated with GPRL after three washes was 4.8% that of the peak height after one wash. It was not possible to determine the washout of GPRF [SEQ ID NO:9] due to insufficient resolution on capillary electrophoresis. Additionally, LPK washed out more slowly in that its peak height after three washes was 10% that of the same peak height after one wash. The relatively low affinity of GPRL [SEQ ID NO:8] was demonstrated in the fibrin polymerization assay. It was found that, while GPRL [SEQ ID NO:8] inhibited fibrin polymerization, its affinity was less than that of GPR or GPRP [SEQ ID NO:6]. The tetrapeptide GPRF [SEQ ID NO:9] was less active than GPRL [SEQ ID NO:8]. Finally, the hexapeptide DKPDNF [SEQ ID NO:3] washed out very slowly in that its peak height after three washes was 48% of that after one wash.

EXAMPLE 6

Monitoring the Synthesis and Binding of Functional Peptides to the Receptor Macromolecule In the initial reaction, we will examine the ability of a peptide scrambling system to generate peptides which will bind to fibrinogen at the GPRP binding site. This system should serve as a useful initial model of the monitoring system as fibrinogen-GPRP binding parameters heave been defined and we have on hand several analogues of various affinities. A potential complication of this system is the fact that fibrinogen has two binding sites for GPRP. In order to simplify analysis, fragment D from fibrinogen (one GPRP binding site with a binding affinity equivalent to that of intact fibrinogen) will be employed.

The initial starting conditions will consist of GPRP complexed to agarose beads. GPRP has an affinity ($K_{GPRP}$) of $2\times10^{-5}$M for fragment D. If we employ an immobilized GPRP bead concentration of $2\times10^{-4}$M, then, from the law of mass action, approximately 91% of fragment D will be bound to the GPRP complexed agarose beads (Equation 1).

$$\text{Fraction bound} = GPRP/(GPRP + K_{GPRP}) \quad \text{Equation 1:}$$

If the fragment D concentration ($R_1$) is set at $2\times10^{-5}$M then 91% or $1.8\times10^{-5}$M will be bound and $1.8\times10^{-6}$M will be free. This free fragment D concentration would constitute the baseline signal of free receptor. Free fragment D could be measured easily if it is radiolabeled, e.g., with $^{125}$I, prior to inclusion in this assay.

The immobilized GRPR-fragment D binding system will then be dialyzed against a peptide scrambling reaction. If the peptide scrambling reaction is able to synthesize a peptide (P*) at a concentration of $2\times10^{-6}$M with an affinity ($K_{P*}$) to the GRPR-fragment D binding site of $2\times10^{-5}$M, then, from equation 2, the concentration of receptor with P* (R·P*) will be 2×10−7M.

$$RP^* = (P^* \times Rt)/(P^* + K_{p^*} \cdot (1 + GPRP/K_{GPRP})) \quad \text{Equation 2:}$$

Given an equal probability of synthesized peptide interacting with complexed fragment D as with free fragment D, the free receptor concentration should increase by a factor of $0.91\times(2\times10^{-7}$M). This value is well above the lower limit of detection for free iodinated fragment D. Thus, an increase in free iodinated fragment D would serve as a monitor for the synthesis of peptides with higher affinity for the GPRP binding site on fragment D.

In summary, an inherent advantage of this system is related to the increased sensitivity for measuring the formation of peptides which bind to the relevant receptor binding site. Using the more conventional approach, bound material is separated and collected using reversed-phase HPLC and capillary electrophoresis; the amino acid sequence of the collected material is then determined. Amino acid sequencing requires approximately $1 \times 10^{-11}$ moles of peptide. By utilizing radioiodinated receptor, the monitoring system can theoretically measure changes in receptor-bound peptide as small as $2 \times 10^{-16}$ moles. This could represent an increase in sensitivity of almost 5 orders of magnitude, and therefore would result in a decrease in the amount of receptor needed, a decrease in the time necessary to measure P*, and an increased ability to measure the effects of different incubation conditions quickly.

EXAMPLE 7

Monitoring the Scrambling Reaction

The streptavidin-biotin complex is characterized by an extremely low $K_d$ of approximately $10^{-15}$M. Biotin analogues like imminobiotin and desthiobiotin have been synthesized that have $K_d$'s of approximately $10^{-8}$M and $10^{-13}$M respectively. The interaction between streptavidin and imminobiotin is the basis of the use of the complex in a monitoring type of reaction.

In the present case, the monitoring concept is based on the assumption that ligands which compete in affinity with imminobiotin (immobilized on agarose) will displace streptavidin from the complex. Streptavidin freed from the complex in this reaction is quantitated using radioactive biotin. A large number of reactions can be easily tested for their ability to generate ligands that compete with imminobiotin for the binding site on streptavidin. Experiments conducted in the laboratory showed that stock peptides do not displace streptavidin but that known ligands like desthiobiotin do.

The monitoring concept was applied to test the ability of the RLI precess to provide amplification of peptides with high specificity and affinity for the receptor. In the present situation, the displacement should be greater in reactions run in the presence of streptavidin than in reactions run in the absence of streptavidin and then spiked with streptavidin.

Materials and Methods

The tripeptide, HPQ was synthesized, and purified by HPLC. The stock peptides were prepared by hydrolyzing BSA using trypsin. Other chemicals were obtained commercially. (Proteinase K from Boehringer Mannheim; Iminobiotin-Agarose (IbAg) and Streptavidin from Sigma Chemical Company). The $^{14}$C-labeled Biotin was purchased from Amersham and diluted 10 fold. The buffer used in the reactions was 0.05M sodium borate, 0.5M NaCl adjusted to pH 9 with 0.1M monobasic potassium phosphate.

A stock solution of streptavidin was made containing 2 mg of streptavidin in 1 mL of buffer. The streptavidin-iminobiotin-agarose (SA-IbAg) complex was prepared by adding 0.18 mL of streptavidin stock solution to 0.66 mL of IbAg and the volume adjusted to 5.82 mL using the pH 9 buffer. This was mixed for 6 hrs. by shaking.

The reactions were carried out in a five-cell dialyzer (Spectrum) using Spectra/Por 3 membrane discs (Spectrum) of MWCO 3500 Da. Membranes for the five-cell dialyzer were conditioned according to the procedure supplied by the manufacturer. Each cell of the five-cell dialyzer is divided into two chambers by the membrane—the receptor chamber and the scrambling reaction chamber. The volume of each chamber is about 1.3 mL.

A reaction was prepared using 82 mg of stock peptide (SP) and 16.2 mg of proteinase K (E) and the volume adjusted to 6 mL with buffer. To 3 mL of the reaction was added 14.8 mgs of HPQ.

The five cells of the dialyzer were filled according to Table 7.

Results

The average of three experiments are shown in Table 8.

In A and C, the reaction was run in the presence of streptavidin. In B and D, the reactions were run using buffer in place of streptavidin. This was then spiked with the receptor in order to check the displacement. There is greater displacement with conditions A and C, than B and D. The results indicate that the displacement is higher in reactions run in the presence of streptavidin than in reactions run in the absence of streptavidin and then spiked with the receptor. This suggests that streptavidin in the receptor compartment amplifies those peptides with high affinity for streptavidin. It is to be noted that the actual amplification factor is not known, as this calculation requires knowledge of the concentration and affinity of the products responsible for the differential displacement.

TABLE 1

Comparison of Computer Model with Experimental*:

| Peptide Length (amino acid residues) | Mole % (model) | Mole % (experimental) |
|---|---|---|
| Day 2 | | |
| 6–11 | 23.0 | 18.8 |
| 9–11 | 5.9 | 3.6 |
| Day 4 | | |
| 6–11 | 15.2 | 8.9 |
| 9–11 | 5.0 | 1.1 |

*Conditions:
1) Model: @t = o, pure octamer
2) Experimental: @t = O pure BSA
3) Reaction time scale (ordinate) estimated from scrambling reaction of dipeptide and tripeptide employing 250 µM enzyme.

TABLE 2

Average Concentration of a Sequentially Unique Peptide Formed in a Reaction with Initial Substrate 10 mM Octapeptide of Eight Different Amino Acid Residues

| Length | Average Concentration (ng/L) of each Sequentially Unique Peptide if Indicated Length at 200 hr | Peptide |
|---|---|---|
| 7 | 300 | |
| 8 | 50 | |
| 9 | 3 | |

TABLE 3

Fraction of Synthesized Products Formed in a Tripeptide Scrambling Reaction.

| Synthesis Rate/ Hydrolysis Rate (%) | Max. Mole % L = 4 to 8 |
|---|---|
| 0.05 | 0.0274 |
| 0.5 | 0.273 |
| 25.0 | 10.7 |
| 50.0 | 17.5 |
| 75.0 | 23.2 |

TABLE 3-continued

Fraction of Synthesized Products Formed in a Tripeptide Scrambling Reaction.

| Synthesis Rate/Hydrolysis Rate (%) | Max. Mole % L = 4 to 8 |
|---|---|
| 99.5 | 27.4 |
| 100.0 | 27.5 |

TABLE 4

HPLC and CE Retention Times[1] of Peptides of Interest After Scrambling of Peptide Mixture of Example 4

| Peptide | HPLC | CE |
|---|---|---|
| Substrates: | | |
| RD | 3.5 | ND[2] |
| WY | 22.5 | 19.0 |
| GSF | 16 | ND |
| Products: | | |
| RGDW [SEQ ID NO:1] | 21.5 | 14.5 |
| RGDF [SEQ ID NO:10] | 18.5 | ND |
| RGDY [SEQ ID NO:4] | 15 | ND |

[1]Retention times are in minutes
[2]Not determined

TABLE 5

HPLC and CE Retention Times[1] of Peptide of Interest After Scrambling of GPR-Spiked Starting Mixture (Example 5)

| Peptide | HPLC | CE |
|---|---|---|
| GPR | 10 | 10.5 |
| LPK[2] | 12 | 11.8 |
| GPRL [SEQ ID NO:8] | 20 | 11.7 |
| GPRF [SEQ ID NO:9] | 20 | 12.0 |
| DKPDNF [SEQ ID NO:3] | 19.5 | 17.3 |

[1]Retention times are in minutes
[2]LPK is not a scrambled product

TABLE 6

| Target Protein | Lead Peptide | Kd (M) |
|---|---|---|
| GpIIbIIa | GRGDSP [SEQ ID NO:11] (Fb) | $10^{-6}$ |
|  | RGDW [SEQ ID NO:1], RGDF [SEQ ID NO:10] (trigramin, Fb) | $10^{-6}$, $10^{-5}$ |
|  | RGDY [SEQ ID NO:4] (pers.comm.) | $10^{-6}$ |
| Urokinase Receptor | TCVXNKYFSNIHW [SEQ ID NO:12] (hum.) (urokinase) | $10^{-6}$ |
| Gastricsin (hum.) | TTFKRIFLKRMPS [SEQ ID NO:13] (prorenin) | $10^{-6}$ |
| Pepsin (hum.) | RIFLKRMPSIR [SEQ ID NO:14] (prorenin) | $10^{-6}$ |
| CD4 | TNYT [SEQ ID NO:15] | $10^{-6}$ |
| Porcine PLA$_2$ | MLFILIKRSRHF [SEQ ID NO:16] (Polyoma Virus) | $10^{-5}$ |
| Calmodulin | VAITVLVK [SEQ ID NO:17] (Ca$^{2+}$-binding site antisense) | $10^6$ |
| Fibronectin (rat) | WTVPTA [SEQ ID NO:18] (antisense of GAVSTA RGD [SEQ ID NO:19] sequence) | $10^{-6}$ |
| Angiotensin II Receptor | EGVYVHPV [SEQ ID NO:20] (antisense of AII) | $10^{-7}$ |

TABLE 7

| CELL | RECEPTOR CHAMBER (A) | REACTION CHAMBER (B) |
|---|---|---|
| 1 | SA-IbAg complex | SP + E |
| 2 | SA-IbAg complex | HPQ + SP + E |
| 3 | SA-IbAg complex | Buffer |
| 4 | Buffer | SP + E |
| 5 | Buffer | HPQ + SP + E |

TABLE 8

| Assay Mixture | Displacement (20 min.) |
|---|---|
| A. 0.6 mL SA-IbAg complex (receptor chamber-cell 2) + 0.6 mL buffer (reaction chamber-cell 3) | 2.6% |
| B. 0.6 mL SA-IbAg complex (receptor chamber-cell 3) + 0.6 mL buffer (receptor chamber-cell 5) | 0.57% |
| C. 0.6 mL SA-IbAg complex (receptor chamber-cell 1) + 0.6 mL buffer (reaction chamber-cell 3) | 0.26% |
| D. 0.6 mL SA-IbAg complex (receptor chamber-cell 3) + 0.6 mL buffer (receptor chamber-cell 4) | 0.03% |

What is claimed is:

1. A method of identifying peptides which bind specifically to a predetermined target, comprising the steps of:

(a) subjecting a mixture initially comprising a starting protein and/or plurality of starting peptides to conditions, comprising proteolytic enzyme exposure, under which the starting proteins and/or peptides and derivatives thereof can undergo both random degradation into smaller peptide and free amino acid derivatives, and random recombination of the starting proteins and/or peptides, and/or their derivatives, into new peptides, whereby the component amino acids of the starting mixture are scrambled to generate a diverse population of scrambled peptides of different sequences, said scrambled peptides not being characterized by a predetermined amino acid sequence;

(b) allowing the starting peptides, if any, peptide fragments of the starting peptides and/or proteins, and scrambled peptides, to compete with each ocher to bind to the target to form a specifically bound peptide-target complex;

(c) protecting only those competing peptides which are bound to the target from further scrambling;

(d) recovering the specifically bound peptide from a peptide-target complex;

(e) sequencing a recovered specifically bound peptide, wherein the improvement comprises monitoring the formation of peptide-target complex, said monitoring effected directly or indirectly, intermittently or continuously, during the scrambling reaction, by a monitoring method comprising incubating the target with a labeled ligand specific for the target, which ligand is disclaceable by one or more scrambled peptides, and measuring the concentration of free-labeled ligand, target-bound ligand, or unlabeled reagent.

2. The method of claim 1 in which both the ligand and the target are soluble.

3. The method of claim 2 in which, in step (e), free labeled ligand, target bound ligand, and unlabeled target are chromatographically separated.

4. The method of claim 2 in which free labeled ligand is measured.

5. The method of claim 2 in which targeted bound ligand is measured.

6. The method of claim 2 in which unlabeled target is measured.

7. The method of claim 2 in which the label is fluorescent and the measurement is spectroscopic and in situ.

8. The method of claim 1 in which the ligand is immobilized.

9. The method of claim 1 in which the receptor is immobilized.

10. The method of claim 1 wherein the proteolytic enzyme is selected from the group consisting of papain, pepsin, bromelin, thermolysin, trypsin, pronase, chymotrypsin, subtilisin and dipeptidyl peptidase IV.

11. The method according to claim 1 wherein the protection from further scrambling is provided by interposing a semipermeable membrane between said enzymes and said target, said membrane being permeable to said peptides and impermeable to said target and said enzymes.

12. The method of claim 11 wherein the semipermeable membrane has a permeability cutoff of about 1–3.5 kDa.

13. the method of claim 1 wherein protection from further scrambling is provided by immobilizing the enzymes in a first zone and the targets in a second, spatially separated zone, the unbound peptides generated by the scrambling reaction being allowed to circulate between the first and second zone.

14. The method of claim 1, further comprising monitoring the peptide size distribution from time to time while the scrambling reaction is in progress.

15. The method of claim 14, further comprising adjusting the peptide size distribution during the course of the scrambling reaction by adding more amino acids, peptides or protein, or by diluting the reaction mixture.

16. The method claim 1 wherein the average length of the peptides of the starting mixture is in the range of 7 to 10 amino acids.

17. The method of claim 1 wherein substantially all of the twenty genetically encoded amino acids are represented in the peptides of the starting mixture.

18. The method of claim 1, wherein the starting mixture is biased in favor of or against certain predetermined amino acids.

19. The method of claim 1, wherein the starting mixture is spiked with a peptide of known sequence and having an affinity of at least about $10^{-4}$ for the target.

20. The method according to claim 1 wherein the specific target is a receptor involved in a physiological process.

21. The method of claim 1, wherein the scrambled peptides are simultaneously screened for affinity for each of a plurality of different targets.

22. The method of claim 1 wherein the target is a macromolecule or a macromolecular complex.

23. The method according to claim 22 wherein the macromolecule or macromolecular complex is fibrinogen, sickle cell hemoglobin, collagenase IV, renin, $GpII_bIII_a$ or phospholipase $A_2$.

24. The method of claim 11 wherein said semipermeable membrane defines a scrambling zone and a binding zone, the target is provided in soluble form but cannot pass the membrane, and the binding of the scrambled peptides to the predetermined target in the binding zone is monitored by:

(i) incubating an insolubilized ligand having a known affinity for the target with said target, prior to commencing the scrambling of step (a), and (ii) whenever it is desired to monitor the binding of the scrambled peptides to the target, sampling the soluble fraction from binding zone and assaying the sample for the presence of the soluble target.

* * * * *